United States Patent
Boor et al.

(10) Patent No.: US 10,285,956 B2
(45) Date of Patent: May 14, 2019

(54) N-(2-AMINOETHYL) ETHANOLAMINE (AEEA) AND ANALOGS TO TREAT HYPERTROPHIC SCARRING AND LIPOSOMAL TOPICAL DELIVERY

(71) Applicant: BOARD OF REGENTS, THE UNIVERSITY OF TEXAS SYSTEM, Austin, TX (US)

(72) Inventors: Paul J. Boor, Galveston, TX (US); Ludwik K. Branski, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 92 days.

(21) Appl. No.: 15/673,917

(22) Filed: Aug. 10, 2017

(65) Prior Publication Data

US 2018/0042866 A1   Feb. 15, 2018

Related U.S. Application Data

(60) Provisional application No. 62/373,836, filed on Aug. 11, 2016.

(51) Int. Cl.
| | | |
|---|---|---|
| A61K 9/127 | (2006.01) | |
| A61K 31/132 | (2006.01) | |
| A61K 9/00 | (2006.01) | |
| A61K 31/133 | (2006.01) | |

(52) U.S. Cl.
CPC .......... *A61K 31/132* (2013.01); *A61K 9/0014* (2013.01); *A61K 9/0019* (2013.01); *A61K 9/0048* (2013.01); *A61K 9/127* (2013.01); *A61K 31/133* (2013.01)

(58) Field of Classification Search
None
See application file for complete search history.

(56) References Cited

U.S. PATENT DOCUMENTS 7,300,916 B2   11/2007   Yasuda et al.
2014/0234250 A1   8/2014   Capone et al.

OTHER PUBLICATIONS

Sylvester, A., et al., Nanoparticles for localized delivery of hyaluronan oligomers towards regenerative repair of elastic matrix. Acta Biomater, 2013. 9(12):9292-302.
Taatjes, D.J., et al., Imaging of collagen type III in fluid by atomic force microscopy. Microsc Res Tech, 1999. 44 (5):347-52.
Taipale, J., et al., "Latent transforming growth factor-beta 1 and its binding protein are components of extracellular matrix microfibrils." J Histochem Cytochem, 1996. 44(8):875-89.
Travis, T.E., et al., "Biphasic Presence of Fibrocytes in a Porcine Hypertrophic Scar Model." J Burn Care Res, 2014.
Ulrich, D., et al., "Matrix metalloproteinases and tissue inhibitors of metalloproteinases in patients with different types of scars and keloids." J Plast Reconstr Aesthet Surg, 2010. 63(6):1015-21.
Wang, L., et al., "Manipulating glutathione-S-transferases may prevent the development of tolerance to nitroglycerin." Cardiovasc Toxicol, 2006. 6(2):131-44.
Woodcock, S.E., et al., "Collagen adsorption and structure on polymer surfaces observed by atomic force microscopy." J Colloid Interface Sci, 2005. 292(1):99-107.
Xu, Y., et al., "Dissecting aortic aneurysm induced by N-(2-aminoethyl) ethanolamine in rat: Role of defective collagen luring development." Birth Defects Res a Clin Mol Teratol, 2014. 100(12):924-33.
Zhang K. et al., "Increased types I and III collagen and transforming growth factor-beta 1 mRNA and protein in hypertrophic burn scar." J Invest Dermatol, 1995. 104(5):750-4.
Zhang, Z., et al., "Smad ubiquitination regulatory factor 2 expression is enhanced in hypertrophic scar fibroblasts from burned children." Burns, 2012. 38(2):236-46.
Zork, N.M., et al. "A systematic evaluation of collagen cross-links in the human cervix." Am J Obstet Gynecol, 2014. 212(3):e1-e8.
Agarwal, S.K., "Integrins and cadherins as therapeutic targets in fibrosis." Front Pharmacol, 2014. 5:131.
Annes, J.P., et al., "Making sense of latent TGF13 activation." J Cell Sci, 2003. 116(Pt 2):217-24.
Aoyagi, M., et al., "Smooth muscle cell proliferation, elastin formation, and tropoelastin transcripts during the development of intimal thickening in rabbit carotid arteries after endothelial denudation." Histochem Cell Biol, 1997. 107(1):11-7.
Asano, Y., et al., "Increased expression of integrin $\alpha v r \beta 5$ induces the myofibroblastic differentiation of dermal fibroblasts." Am J Pathol, 2006. 168(2):499-510.
Asano, Y., et al., "Involvement of $\alpha v \beta 5$ integrin in the establishment of autocrine TGF-$\beta$ signaling in dermal fibroblasts derived from localized scleroderma." J Invest Dermatol, 2006. 126(8):1761-9.
Barnes, J.L., et al., "Myofibroblast differentiation during fibrosis: role of NAD(P)H oxidases." Kidney Int, 2011. 79 (9):944-56.
Boo, S., et al., "Integrins as Modulators of Transforming Growth Factor Beta Signaling in Dermal Fibroblasts During Skin Regeneration After Injury." Adv Wound Care, 2013. 2(5):238-246.
Bourget, J.M., et al., "Human fibroblast-derived ECM as a scaffold for vascular tissue engineering." Biomaterials, 2012. 33(36):9205-13.
Branski, L.K., et al., "A porcine model of full-thickness burn, excision and skin autografting." Burns, 2008. 34 (8)1119-27.
Caputo, I., et al., "An acetic acid-based extraction method to obtain high quality collagen from archeological bone remains." Anal Biochem, 2012. 421(1):92-6.
Chan, Q.E., et al., "The correlation between time to skin grafting and hypertrophic scarring following an acute contact burn in a porcine model." J Burn Care Res, 2012. 33(2):e43-8.
Chen, Z., et al., "N-(2-Aminoethyl) Ethanolamine-Induced Morphological, Biochemical, and Biophysical Alterations in Vascular Matrix Associated With Dissecting Aortic Aneurysm." Toxicol Sci, 2015. 148(2):421-32.

(Continued)

*Primary Examiner* — Nannette Holloman
(74) *Attorney, Agent, or Firm* — Chalker Flores, LLP; Edwin S. Flores

(57) ABSTRACT

The present invention includes pharmaceutical liposome formulation thereof comprising a N-(2-aminoethyl) ethanolamine (AEEA) and/or active analogs thereof in a liposome, wherein the N-(2-aminoethyl) ethanolamine (AEEA) and/or active analogs thereof are provided in an amount sufficient to treat or reduce scarring of the skin or eye.

35 Claims, 4 Drawing Sheets

(56) References Cited

OTHER PUBLICATIONS

Creemers, L.B., et al., "Microassay for the assessment of low levels of hydroxyproline." Biotechniques, 1997. 22 (4):656-8.
Csiszar, K., "Lysyl oxidases: a novel multifunctional amine oxidase family." Prog Nucleic Acid Res Mol Biol, 2001. 70:1-32.
Dallas, S.L., et al., "Fibronectin regulates latent transforming growth factor-beta (TGF beta) by controlling matrix assembly of latent TGF beta-binding protein-1." J Biol Chem, 2005. 280(19):18871-80.
Davidson, J.M., et al., "Ascorbate differentially regulates elastin and collagen biosynthesis in vascular smooth muscle cells and skin fibroblasts by pretranslational mechanisms." J Biol Chem, 1997. 272(1):345-52.
Domergue, S., et al., "Advances in Research in Animal Models of Burn-Related Hypertrophic Scarring." J Burn Care Res, 2014. 36(5):e259-e266.
Florin, E.L., et al., "Adhesion forces between individual ligand-receptor pairs." Science, 1994. 264(5157):415-7.
Gacheru, S.N., et al., "Structural and catalytic properties of copper in lysyl oxidase." J Biol Chem, 1990. 265 (31):19022-7.
Goh, C.L., "Occupational dermatitis from soldering flux among workers in the electronics industry." Contact Dermatitis, 1985. 13(2):85-90.
Gong, B., et al., "Chemical-induced, nonlethal, developmental model of dissecting aortic aneurysm." Birth Defects Res A Clin Mol Teratol, 2006. 76(1):29-38.
Hinz, B., et al., "Cell-matrix and cell-cell contacts of myofibroblasts: role in connective tissue remodeling." Thromb Haemost, 2003. 90(6):993-1002.
Hinz, B., "The extracellular matrix and transforming growth factor-beta1: Tale of a strained relationship." Matrix Biol, 2015.47:54-65.
Ingber, D.E., "Integrins, tensegrity, and mechanotransduction." Gravit Space Biol Bull, 1997. 10(2):49-55.
Kagan, H.M. et al., "Lysyl oxidase: properties, specificity, and biological roles inside and outside of the cell." J Cell Biochem, 2003. 88(4):660-72.
Kielty, C.M. et al., "Abnormal fibrillin assembly by dermal fibroblasts from two patients with Marfan syndrome." J Cell Biol, 1994. 124(6):997-1004.
Kliment, C.R., et al., "A novel method for accurate collagen and biochemical assessment of pulmonary tissue utilizing ane animal." Int J Clin Exp Pathol, 2011.4(4):349.
Langford, S.D. et al., "Developmental vasculotoxicity associated with inhibition of semicarbazide-sensitive amine oxidase." Toxicol Appl Pharmacol, 1999. 155(3):237-44.
Langford, S.D., et al., "Cultured rat vascular smooth muscle cells are resistant to methylamine toxicity: no correlation to semicarbazide-sensitive amine oxidase." Cardiovasc Toxicol, 2001. 1(1):51-60.
Langford, S.D., et al., "Semicarbazide-sensitive amine oxidase and extracellular matrix deposition by smooth-muscle cells." Cardiovasc Toxicol, 2002. 2(2):141-50.

Leask, A., "Potential therapeutic targets for cardiac fibrosis: TGFbeta, angiotensin, endothelin, CCN2, and PDGF, partners in fibroblast activation." Circ Res, 2010. 106(11):1675-80.
Li, C. et al., "MiR-10a and miR-181c regulate collagen type I generation in hypertrophic scars by targeting PAI-1 and uPA." FEBS Lett, 2015. 589(3):380-9.
Li, Z.J., et al., "The application of the starfish hatching enzyme for the improvement of scar and keloid based on the fibroblast-populated collagen lattice." Appl Biochem Biotechnol, 2014. 173(4):989-1002.
Lopez, et al., "Role of lysyl oxidase in myocardial fibrosis: from basic science to clinical aspects." Am J Physiol Heart Circ Physiol, 2010. 299(1):H1-9.
Lucero, H.A., et al., "Lysyl oxidase: an oxidative enzyme and effector of cell function." Cell Mol Life Sci, 2006. 63 (19-20):2304-16.
Marko, J.F., et al., "Statistical mechanics of supercoiled DNA." Phys Rev E Stat Phys Plasmas Fluids Relat Interdiscip Topics, 1995. 52(3):2912-2938.
Mithieux, S.M., et al., "Synthetic elastin hydrogels derived from massive elastic assemblies of self-organized human protein monomers." Biomaterials, 2004.25(20):4921-7.
Nedelec, B., et al., "Control of wound contraction. Basic and clinical features." Hand Clin, 2000. 16(2):289-302.
Nunes, I., et al., "Latent transforming growth factor-beta binding protein domains involved in activation and transglutaminase-dependent cross-linking of latent transforming growth factor-β" J Cell Biol, 1997. 136(5):1151-63.
Oberhauser, A.F., et al., "The molecular elasticity of the extracellular matrix protein tenascin." Nature, 1998. 393 (6681)181-5.
Oberhauser, A.F., et al., "Single protein misfolding events captured by atomic force microscopy." Nat Struct Biol, 1999. 6(11)1025-8.
Oberhauser, A.F., et al., "Stepwise unfolding of titin under force-clamp atomic force microscopy." Proc Natl Acad Sci U S A, 2001. 98(2):468-72.
Oberhauser, A.F., et al., "The mechanical hierarchies of fibronectin observed with single-molecule AFM". J Mol Biol, 2002. 319(2):433-47.
Palamakumbura, A.H., et al., "A fluorometric assay for detection of lysyl oxidase enzyme activity in biological samples." Anal Biochem, 2002. 300(2):245-51.
Penn, J.W., et al., "The role of the TGF-β family in wound healing, burns and scarring: a review." Int J Burns Trauma, 2012. 2(1)18-28.
Rabello, F.B., et al., "Update on hypertrophic scar treatment." Clinics (Sao Paulo), 2014.69(8):565-73.
Raghunath, M., et al., "Carboxy-terminal conversion of profibrillin to fibrillin at a basic site by PACE/furin-like activity required for incorporation in the matrix." J Cell Sci, 1999. 112 ( Pt 7):1093-100.
Rhett, J.M., et al., "Novel therapies for scar reduction and regenerative healing of skin wounds." Trends Biotechnol, 2008. 26(4):173-80.
Sarrazy, V., et al., "Integrins αvβ5 and αvβ3 promote latent TGF-β1 activation by human cardiac fibroblast contraction." Cardiovasc Res, 2014. 102(3):407-17.
Slemp, A.E., et al., "Keloids and scars: a review of keloids and scars, their pathogenesis, risk factors, and management" Curr Opin Pediatr, 2006. 18(4):396-402.

N-(2-AMINOETHYL) ETHANOLAMINE (AEEA) AND ANALOGS TO TREAT HYPERTROPHIC SCARRING AND LIPOSOMAL TOPICAL DELIVERY

CROSS-REFERENCE TO RELATED APPLICATIONS

This non-provisional Patent Application claims priority to U.S. Provisional Patent Application Ser. No. 62/373,836, filed on Aug. 11, 2016, entitled "N-(2-Aminoetheyl) Ethanolamine (AEEA) and Analogs to Treat Hypertrophic Scarring and Liposomal Topical Delivery," the contents of which is incorporated by reference herein in its entirety.

STATEMENT OF FEDERALLY FUNDED RESEARCH

None.

TECHNICAL FIELD OF THE INVENTION

The present invention relates in general to the field of scarring, and more particularly, to the use of AEEA and analogs thereof for the treatment of hypertrophic scarring and liposomal delivery thereof.

BACKGROUND OF THE INVENTION

Without limiting the scope of the invention, its background is described in connection with scarring.

Hypertrophic scar is a common, important medical problem in any healing process; however it is a critical determinant of outcomes in recovery from major burns. Up to 90% of severely burned patients have hypertrophic scarring (estimated at nearly a million/year).

More specifically, hypertrophic scars (HS) are exuberant, pathological growths of scar tissue resulting in bulky, inelastic masses that restrict movement and cause a multitude of morbidities. However, there is little effective treatment for HS, other than surgical revision, and this problem remains a major issue in burn wound therapy.

One such patent is U.S. Pat. No. 7,300,916, issued to Yasuda, et al. entitled, "Preventives/remedies for thickened scar, keloid or chronic arthritic diseases." Briefly, these inventors are said to teach a pharmaceutical preparation for preventing and/or treating hypertrophic scars, keloid or chronic arthritic diseases comprising as an effective component an erythropoietin antagonist. Specifically, a pharmaceutical preparation is provided for preventing and/or treating hypertrophic scars, keloid or chronic arthritic diseases comprising as an effective component an erythropoietin antagonist such as an anti-erythropoietin antibody, an erythropoietin receptor protein, etc. It is said that the pharmaceutical preparation has excellent prophylactic and/or therapeutic effects on collagenous hyperproliferation such as hypertrophic scars, keloid, etc., or chronic arthritic diseases such as rheumatoid arthritis, etc.

Another such approach is taught in U.S. Patent Publication No. 2014/0234250, filed by Capone, et al., and entitled "Methods and Compositions for Improving Appearance and Formation of Scar Tissue." Briefly, the invention is said to include methods and compositions for degrading collagen in mammalian skin, thereby improving the appearance and/or reducing the size of a closed wound, which may be a scar or a keloid and cellulite or other conditions wherein excessive collagen is a problem with a composition comprising at least one ureido polymer in an amount effective to degrade said collagen.

SUMMARY OF THE INVENTION

In one embodiment, the present invention includes a pharmaceutical liposome formulation thereof comprising: a N-(2-aminoethyl) ethanolamine (AEEA) and/or active analogs thereof in a liposome, wherein the N-(2-aminoethyl) ethanolamine (AEEA) and/or active analogs thereof are provided in an amount sufficient to treat or reduce scarring of the skin or eye. In one aspect, the AEEA and/or active analogs thereof are provided in a low dose, which is a dose that is effective to treat or reduce scarring of the skin and that reduces or does not otherwise cause dermatitis. In another aspect, the pH of the formulation is adjusted to reduce or prevent dermatitis. In another aspect, the scarring is defined further as hypertrophic scarring, scarring from burns, keloid scarring, scars that result from pimples, body piercings, tattooing, surgery, cuts and/or burns, scars associated with Classic Type Ehlers-Danlos syndrome, or scars from thermal, radiation, or traumatic skin or eye injuries that involve the deep layers of the dermis. In another aspect, the active analogs of AEEA are selected from at least one of:

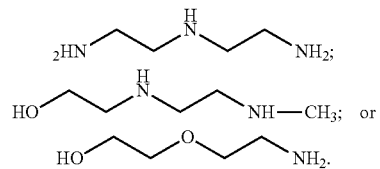

In another aspect, the liposomes comprise one or more lipids selected from glycerophospholipids, phosphatidylcholines, phosphatidylglycerols, phosphatidylethanolamines, phosphatidylserines, phosphatidic acids, phosphatidylinositols, dimyristoyl phosphatidylglycerols, dimyristoyl phosphatidylcholines, di stearoylphosphatidylethanolamines, di stearoylphosphatidylcholine, dipalmitoylphosphatidylglycerol, egg-phosphatidylcholine, egg-phosphatidylglycerol, dimyristyloxy-propyl-3-dimethyl-hydroxy ethyl ammoniums, dioleoyphosphatidyl cholines, cholesterols, cholesterol derivatives, ceramides, monosialogangliosides, sphingomyelins, cardiolipins, long chain fatty acids or mixtures thereof salts or a mixture thereof. In another aspect, the liposomes comprise one or more skin-related lipids. In another aspect, the liposomes are further defined as comprising at least one of: a lamellarity selected from uni-, oligo-, and multilamellar vesicles; a size that is small, intermediate, or large; are reverse phase evaporation vesicles (VETs); are PEGylated; are targeted liposomes; and/or are stealthed liposomes. In another aspect, the formulation is incorporated into a wound dressing. In another aspect, the formulation is adapted for ocular administration for the treatment of eye fibrosis selected from at least one of: exophthalmos of Grave's disease, proliferative vitreoretinopathy, anterior capsule cataract, corneal fibrosis, corneal scarring due to surgery, trabeculectomy-induced fibrosis, progressive subretinal fibrosis, and multifocal granulomatous chorioretinitis. In another aspect, the formulation further comprises at least one of: a stabilizer, a penetration enhancer, a humectant, a deodorant, an aroma modifier, a sun screening agent, a sunless tanning agent, a pH adjusting agent, a sun blocking agent, a chelating agent, a preservative, an emulsifier, an occlusive agent, an emollient, a thickener, a solubilizing agent, an anti-irritant, or a colorant. In another aspect, the formulation further comprises at least one penetration enhancer selected from at least one of: propylene glycol (PG), polyethylene glycol (PEG), dimethyl formamide (DMF), allantoin, urazole, N,N-dimethylacetamide (DMA), decylmethylsulfoxide, polyethylene glycol monolaurate (PEGML), propylene glycol monolaurate (PGML), Phosal glycerol monolaurate (GML), lecithin, 1-substituted azacycloheptan-2-ones, alcohols, or vegetable oils. In another aspect, the formulation is adapted for topical or ocular administration in the form of a cream, an ointment, a paste, a gel, a lotion, a milk, a suspension, a serum, a solution, an aerosol, a spray, a foam, a shampoo, a mousse, a serum, a swab, a pledget, a pad, a tincture, a patch, a dressing, an adhesive bandage, an oil, or drops.

In another embodiment, the present invention includes a method of preventing or treating scar formation of the skin or eyes by administering a N-(2-aminoethyl) ethanolamine (AEEA) and/or active analogs thereof in a liposome, wherein the N-(2-aminoethyl) ethanolamine (AEEA) and/or active analogs thereof are provided in an amount sufficient to treat or reduce scarring of the skin or eye to a subject in need thereof. In one aspect, further comprising the step of providing the AEEA and/or active analogs thereof in a low dose, which is a dose that is effective to treat or reduce scarring of the skin and that reduces or does not otherwise cause dermatitis. In one aspect, the method further comprises the step of adjusting the pH of the formulation to reduce or prevent dermatitis. In another aspect, the scarring is defined further as hypertrophic scarring, scarring from burns, keloid scarring, scars that result from pimples, body piercings, tattooing, surgery, cuts and/or burns, scars associated with Classic Type Ehlers-Danlos syndrome, or scars from thermal, radiation, or traumatic skin or eye injuries that involve the deep layers of the dermis. In another aspect, the active analogs of AEEA are selected from at least one of:

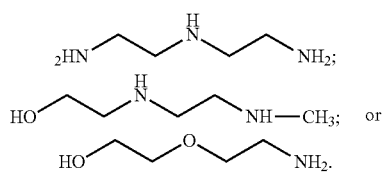

In another aspect, the liposomes comprise one or more lipids selected from glycerophospholipids, phosphatidylcholines, phosphatidylglycerols, phosphatidylethanolamines, phosphatidylserines, phosphatidic acids, phosphatidylinositols, dimyristoyl phosphatidylglycerols, dimyristoyl phosphatidylcholines, di stearoylphosphatidylethanolamines, di stearoylphosphatidylcholine, dipalmitoylphosphatidylglycerol, egg-phosphatidylcholine, egg-phosphatidylglycerol, dimyristyloxy-propyl-3-dimethyl-hydroxy ethyl ammoniums, dioleoyphosphatidyl cholines, cholesterols, cholesterol derivatives, ceramides, monosialogangliosides, sphingomyelins, cardiolipins, long chain fatty acids or mixtures thereof salts or a mixture thereof. In another aspect, the liposomes comprise one or more skin-related lipids. In another aspect, the liposomes comprise at least one of: a lamellarity selected from uni-, oligo-, and multi-lamellar vesicles; a size that is small, intermediate, or large; are reverse phase evaporation vesicles (VETs); are PEGylated; are targeted liposomes; and/or are stealthed liposomes. In another aspect, the method further comprises the step of incorporating the formulation into a wound dressing. In another aspect, the method further comprises the step of adapting the formulation for ocular administration for the treatment of eye fibrosis comprises a condition selected from the group consisting of: exophthalmos of Grave's disease, proliferative vitreoretinopathy, anterior capsule cataract, corneal fibrosis, corneal scarring due to surgery, trabeculectomy-induced fibrosis, progressive subretinal fibrosis, and multi-focal granulomatous chorioretinitis. In another aspect, the method further comprises the step of adding at least one of: a stabilizer, a penetration enhancer, a humectant, a deodorant, an aroma modifier, a sun screening agent, a sunless tanning agent, a pH adjusting agent, a sun blocking agent, a chelating agent, a preservative, an emulsifier, an occlusive agent, an emollient, a thickener, a solubilizing agent, an anti-irritant, or a colorant. In another aspect, the method further comprises adding at least one penetration enhancer selected from at least one of propylene glycol (PG), polyethylene glycol (PEG), dimethyl formamide (DMF), allantoin, urazole, N,N-dimethylacetamide (DMA), decylmethylsulfoxide, polyethylene glycol monolaurate (PEGML), propylene glycol monolaurate (PGML), Phosal glycerol monolaurate (GML), lecithin, 1-substituted azacycloheptan-2-ones, alcohols, or vegetable oils. In another aspect, the method further comprises making a formulation for topical or ocular administration in the form of a cream, an ointment, a paste, a gel, a lotion, a milk, a suspension, a serum, a solution, an aerosol, a spray, a foam, a shampoo, a mousse, a serum, a swab, a pledget, a pad, a tincture, a patch, a dressing, an adhesive bandage, an oil, or drops.

Yet another embodiment of the present invention, includes a method for treating or preventing scarring of the skin or eye, comprising: identifying a human or animal subject in need of prevention or treatment scarring of the skin or eye; and providing the subject with a topical or ocular formulation comprising a therapeutically effective amount of a N-(2-aminoethyl) ethanolamine (AEEA) and/or active analogs thereof in a liposome in an amount sufficient for treating a wound to a surface tissue or a symptom thereof.

Another embodiment of the present invention, includes a method of making a formulation treating or preventing scarring of the skin or eye when provided to a subject comprising: obtaining a therapeutically effective amount of a N-(2-aminoethyl) ethanolamine (AEEA) and/or active analogs thereof; and mixing the N-(2-aminoethyl) ethanolamine (AEEA) and/or active analogs thereof in with a vehicle adapted for topical administration. In one aspect, the method further comprises the step of adapting the vehicle for topical administration is defined further as comprising one or more bio-compatible polymers, one or more solvents and at least one of the N-(2-aminoethyl) ethanolamine (AEEA) and/or active analogs thereof. In another aspect, the vehicle adapted for topical administration is defined further as comprising one or more bio-compatible polymers comprise at least one or poly(lactic-co-glycolic acid) (PLGA), poly (lactic acid), polylactide (PLA), and poly-L-lactide-co-ε-caprolactone (PLCL). In another aspect, the vehicle adapted for topical administration is defined further as comprising a lipid and the lipid is formed into a liposome by: mixing a lipid aqueous phase with one or more lipids in the presence of the N-(2-aminoethyl) ethanolamine (AEEA) and/or active analogs thereof; mixing the organic phase with the lipid aqueous phase, whereby an emulsion is formed; and incubating the emulsion under conditions that cause the self-assembly of liposome loaded with the N-(2-aminoethyl) ethanolamine (AEEA) and/or active analogs thereof. In another aspect, the method further comprising the step of mixing the organic phase with the lipid aqueous phase comprises at least one of stirring the organic phase into the lipid aqueous phase, mixing the organic phase with the lipid aqueous phase comprises vortexing, or mixing the organic phase with the lipid aqueous phase further comprises sonicating. In another aspect, the vehicle adapted for topical administration is defined further as comprising one or more lipids formed into liposomes, wherein the lipids are selected from at least one of glycerophospholipids, phosphatidylcholines, phosphatidylglycerols, phosphatidylethanolamines, phosphatidylserines, phosphatidic acids, phosphatidylinositols, dimyristoyl phosphatidylglycerols, dimyristoyl phosphatidylcholines, di stearoylphosphatidylethanolamines, di stearoylphosphatidylcholine, dipalmitoylphosphatidylglycerol, egg-phosphatidylcholine, egg-phosphatidylglycerol, dimyristyloxy-propyl-3-dimethyl-hydroxy ethyl ammoniums, dioleoyphosphatidyl cholines, cholesterols, cholesterol derivatives, ceramides, monosialogangliosides, sphingomyelins, cardiolipins, long chain fatty acids or mixtures thereof salts or a mixture thereof. In another aspect, the vehicle adapted for topical administration is defined further as comprising liposomes that comprise one or more skin-related lipids. In another aspect, the vehicle adapted for topical administration is defined further as comprising liposomes that comprise at least one of: a lamellarity selected from uni-, oligo-, and multi-lamellar vesicles; a size that is small, intermediate, or large; are reverse phase evaporation vesicles (VETs); are PEGylated; are targeted liposomes; and/or are stealthed liposomes. In another aspect, the method further comprises the step of incorporating the formulation into a wound dressing. In another aspect, the method further comprises the step of adapting the formulation for ocular administration for the treatment of eye fibrosis comprises a condition selected from the group consisting of: exophthalmos of Grave's disease, proliferative vitreoretinopathy, anterior capsule cataract, corneal fibrosis, corneal scarring due to surgery, trabeculectomy-induced fibrosis, progressive subretinal fibrosis, and multifocal granulomatous chorioretinitis. In another aspect, the method further comprises the step of adding at least one of: a stabilizer, a penetration enhancer, a humectant, a deodorant, an aroma modifier, a sun screening agent, a sunless tanning agent, a pH adjusting agent, a sun blocking agent, a chelating agent, a preservative, an emulsifier, an occlusive agent, an emollient, a thickener, a solubilizing agent, an anti-irritant, or a colorant. In another aspect, the method further comprises adding at least one penetration enhancer selected from at least one of propylene glycol (PG), polyethylene glycol (PEG), dimethyl formamide (DMF), allantoin, urazole, N,N-dimethylacetamide (DMA), decylmethylsulfoxide, polyethylene glycol monolaurate (PEGML), propylene glycol monolaurate (PGML), Phosal glycerol monolaurate (GML), lecithin, 1-substituted azacycloheptan-2-ones, alcohols, or vegetable oils. In another aspect, the method further comprises making a formulation for topical or ocular administration in the form of a cream, an ointment, a paste, a gel, a lotion, a milk, a suspension, a serum, a solution, an aerosol, a spray, a foam, a shampoo, a mousse, a serum, a swab, a pledget, a pad, a tincture, a patch, a dressing, an adhesive bandage, an oil, or drops.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
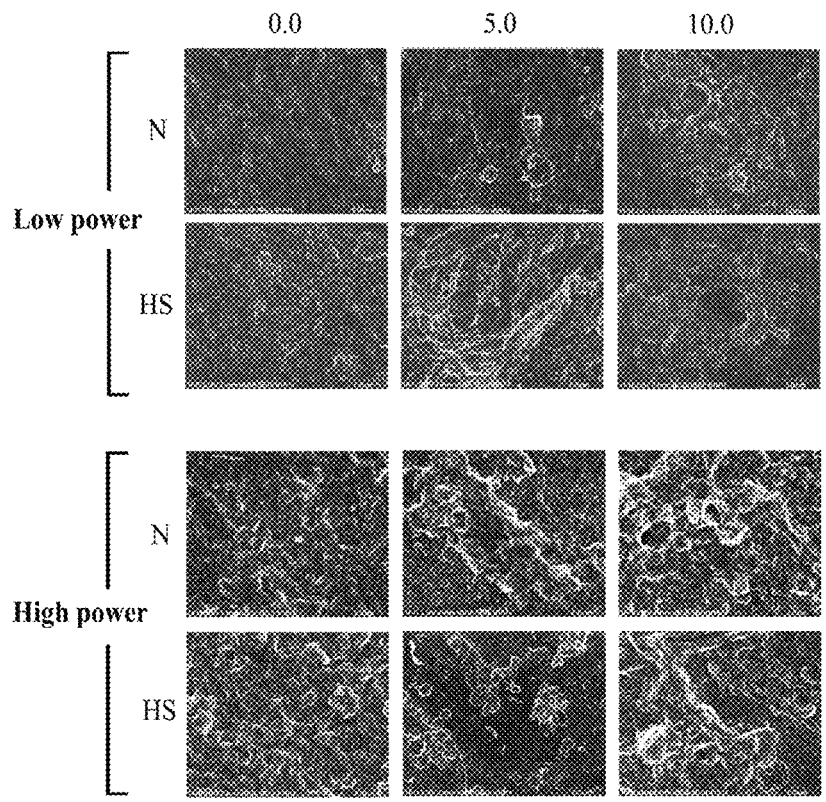
FIG. 1 is a scanning EM (SEM) of interstitial matrix (skin fibroblasts removed) shows marked irregularities, "pits" in matrix, similar to findings in VSMCs in previous studies; N-(2-aminoethyl) ethanolamine (AEEA): 0, 5, 10 mM; Low power X6K; High power X20K.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The matrix produced by skin fibroblastic cells in the healing process is a complex milieu composed of the major structural proteins (mainly collagen and elastin) and a host of other molecules including signaling, enzymatic, and modifying or modulating molecules. There has been little effective therapeutic treatment for hypertrophic scarring, which requires frequent surgical revision. The problem of hypertrophic scarring remains a major issue in burn wound therapy [1, 2]. Therefore, the discovery and development of therapeutic drugs for hypertrophic scarring (HS) is of utmost importance. It is shown herein that N-(2-aminoethyl) ethanolamine (AEEA) and its active analogs affect matrix metabolism during the healing process of the skin. Thus, AEEA and its active analogs can be used for wound healing to beneficially alter the outcomes for countless victims of serious burns in the healing process.

Using scar fibroblast cells from patients with HS, at differing stages of maturation, it was found that cells exposed to N-(2-aminoethyl) ethanolamine (AEEA) produce markedly differing matrix, as observed with scanning EM; at mM doses cells undergo a striking phenotypic change; hypertrophic scar cells appear more sensitive than controls to these effects. Thus, the inventors tested 12 chemical analogs of AEEA, and identified four analogs that were able to show activity in in vitro studies, which are a model system for altering the course of HS in vivo.

Solely for the purpose of explanation, and not a limitation of the present invention, the unique effect of AEEA (and analogs) on collagen production results in a matrix with altered biophysical properties; beneficial effects on scar are likely mediated through matrix molecules involved in cell-matrix interactions including fibronectin, integrins αB and β5, N-cadherin, α-smooth muscle actin (α-SMA), and signaling in scar-forming myofibroblasts including transforming growth factor-β1 (TGF-β1) and TGF-β1/Smad. Further, an established in vivo large animal model of HS, the Duroc pig, can be used to show the effectiveness of AEEA or its active analogs as a clinical therapeutic.

A dosage unit for use of the AEEA and/or its active analogs of the present invention, may be a single compound or mixtures thereof in an excipient, a carrier, a diluent, etc., certain non-limiting examples are described herein below. The AEEA and its active analogs may be mixed with other compounds or salts, and may even form ionic or even covalent bonds. The AEEA and its active analogs of the present invention will generally be administered in a topically, subcutaneous, or intramuscular form, all using dosage forms well known to those of ordinary skill in the pharmaceutical arts. Depending on the particular topical location or method of delivery, different dosage forms, e.g., topical creams, emulsions, serums, powders, tinctures, suspensions, or syrups, may be used to provide the AEEA and its active analogs of the present invention to a patient in need of therapy for scarring, e.g., hypertrophic scarring of the skin.

The AEEA and its active analogs may also be administered as any one of known salt forms. Further, the AEEA and/or its active analogs can be formulated such that they remain on or about the skin and do not penetrate further than the subcutaneous layers, e.g., the formulation can be prepared to prevent transdermal delivery of the AEEA and/or its active analogs as a result of potentially negative effects on metabolism beyond the skin.

For use with the present invention, AEEA and its active analogs are typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices, specifically, topical or dermal applications. Depending on the best location for administration, the AEEA and its active analogs may be formulated to provide, e.g., maximum and/or consistent dosing for treatment of scarring of the skin or eye. While the AEEA and its active analogs may be administered alone, it is common to stabilize the molecule by providing it in a stable salt form mixed with a pharmaceutically acceptable carrier, e.g., liposomes or other lipid carriers, in an emulsion, a serum, or other topical dosage form. The carrier may be solid (e.g., a powder), semi-solid, cream, emulsion, or liquid, depending on the type and/or depth of topical layer selected and/or targeted.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

The AEEA and its active analogs may be administered in the form of liposome delivery systems, e.g., small unilamellar vesicles, large unilamellar vesicles, and multilamellar vesicles, whether charged or uncharged. Liposomes may include one or more: phospholipids (e.g., cholesterol), stearylamine and/or phosphatidylcholines, mixtures thereof, and the like.

The AEEA and its active analogs may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-mide-phenol, or polyethyleneoxide-polylysine substituted with palmitoyl residues, mixtures thereof, and the like. Furthermore, the AEEA and its active analogs may be coupled one or more biodegradable polymers to achieve controlled release of the AEEA and its active analogs, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

Liquid dosage forms for topical administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers. Solutions for topical administration include generally, a water soluble salt of the active ingredient, suitable stabilizing agents, and if necessary, buffering salts. Antioxidizing agents such as sodium bisulfate, sodium sulfite and/or ascorbic acid, either alone or in combination, are suitable stabilizing agents. Citric acid and its salts and sodium EDTA may also be included to increase stability. In addition, topical solutions may include pharmaceutically acceptable preservatives, e.g., benzalkonium chloride, methyl- or propyl-paraben, and/or chlorobutanol. Suitable pharmaceutical carriers are described in Remington's Pharmaceutical Sciences, Mack Publishing Company, a standard reference text in this field, relevant portions incorporated herein by reference.

Non-limiting examples of suitable liquid dosage forms include: solutions or suspensions in water, pharmaceutically acceptable fats and oils, alcohols or other organic solvents, including creams, formulation for topical or ocular administration in the form of a cream, an ointment, a paste, a gel, a lotion, a milk, a suspension, a serum, a solution, an aerosol, a spray, a foam, a shampoo, a mousse, a serum, a swab, a pledget, a pad, a tincture, a patch, a dressing, an adhesive bandage, an oil, or drops. These topical formulations may include emulsions, syrups or elixirs, suspensions, solutions and/or drops adapted for ocular administration. Such liquid dosage forms may contain, for example, suitable solvents, preservatives, emulsifying agents, suspending agents, diluents, sweeteners, thickeners, drops, and melting agents, which will generally be selected to minimize and irritation of the skin.

The present inventors determined the effect of AEEA and its analogs on hypertrophic scarring (HS). First, its possible to evaluate the biophysical alterations of ECM molecules, elaborated by normal scar cells (non-HS) vs. HS cells, in response to AEEA (or analog); this can be accomplished by unique and innovative, state-of-the-art atomic force microscopy, measuring piconewton molecular forces in complex matrices such as ECM. Second, it is possible to understand the mechanisms through which AEEA (or its active analog(s)) affects collagen and matrix production (in normal skin cells vs. HS cells) by examining phenomena known to be involved in HS including myofibroblastic dysregulation of α-SMA, fibronectin, TGF-β1, TGF-β1/Smad signaling, and other potential matrix components as they are revealed; molecular biologic and chemical approaches can be used. The in vivo efficacy of these chemicals (beginning with AEEA) can be tested in a pig model of HS to pave the way for trials in burn patients. Besides assessing parameters of clinical importance (morphology, administration; dose; etc.), the mechanistic and biophysical studies, including atomic force microscopy, will be applied to HS lesions, comparing always to normal scar (non-HS).

Hypertrophic scars are pathologically firm and inelastic, as well as being bulkier than normal scars. These physical properties are important pathologic characteristics that can be defined accurately and rapidly in extracted ECM with the methodology, e.g., atomic force microscopy (AFM). AFM can be used to show how pathologic biophysical properties are changed by AEEA or its active analogs.

Using AFM to assess the physical pathology of the extracellular matrix (ECM) produced in HS is novel and innovative. AFM will be applied in vitro (to ECM elaborated by proliferating skin fibroblastic cells derived from normal healing vs. HS scars (and then to matrix extracted from actual HS from animals). This biophysical methodology can ascertain the effect of AEEA (or analogs) on the firmness and inelasticity that are known to be major clinical characteristics of human HS.

N-(2-aminoethyl) ethanolamine, or AEEA, is an industrial aliphatic amine with enormous worldwide industrial production. Neither AEEA, nor any of the 12 analogs studied to date, have any demonstrated clinical use. In fact, use of AEEA is contraindicated as it is known that AEEA shows dramatic dissecting aortic aneurysms in rat pups born to mother rats exposed in utero. The inventors have shows that AEEA weakens the blood vessel wall by interfering with collagen maturation and interstitial matrix (ECM) metabolism during the laying down of collagen, elastin and matrix proteins that occur during late fetal (near-term) vessel development, when aortic wall is forming [6-8]. However, the aortic wall is very different from other tissue. As such, the inventors first determined if AEEA might also affect scarring, i.e., proliferating fibroblasts or myofibrobasts. It was found that cells exposed to AEEA produce markedly differing collagen and ECM (shown by scanning EM and assessed with Western blotting) and dramatically alter ECM molecules known to be involved in HS. HS cells appear more sensitive than controls to some of these effects. Surprisingly, these findings with HS cells show a significant beneficial effect on HS, especially with regard to collagens.

All data shown herein, FIGS. 1 to 9, were obtained using human scar fibroblast cells from both normal-healing scars and HS at the same stage of healing (from same individual patients). These cells were obtained from children recovering from severe burns [9]; patients' excised skin tissues afforded study of normal scarring skin fibroblasts and skin fibroblasts derived from the clinically evident HS. Embryonic fibroblasts were also studied as an additional control (data not shown). The present inventors found that cells exposed to AEEA (and its active analogs) make a markedly differing matrix, as observed with standard light microscopy (where ECM with cells removed showed marked irregularities; data not shown); this finding is dramatically demonstrated by scanning electron microscopy (SEM) (FIGS. 1 and 2).

Figures 2A, 2B:
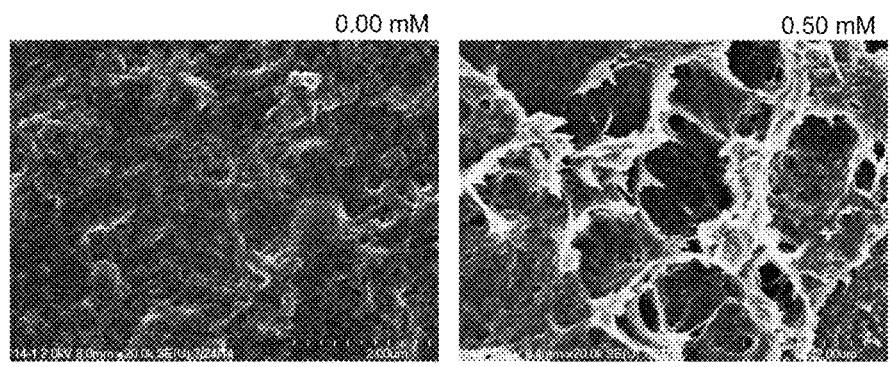
FIGS. 2A and 2B are a SEM of interstitial matrix (cells removed); marked irregularities and defects result in "pits" in matrix, X20K.

FIG. 1 is a scanning EM (SEM) of interstitial matrix (skin fibroblasts removed) shows marked irregularities, "pits" in matrix, similar to findings in VSMCs in previous studies; N-(2-aminoethyl) ethanolamine (AEEA): 0, 5, 10 mM; Low power X6K; High power X20K. FIGS. 2A and 2B are a SEM of interstitial matrix (cells removed); marked irregularities and defects result in "pits" in matrix, X20K. Hypertrophic scar cells appear more sensitive than controls to the AEEA effect with regard to these matrix changes.

Atomic force microscopy is a technique for measuring piconewton molecular forces in samples of purified preparations, such as recombinant proteins (where intramolecular bonding energies may be directly measured) or complex matrix mixtures, as is the case with intercellular matrix, or extracted elastin and collagen preparations. Thus, AFM is a perfect technique to measure physical defects in matrix produced during normal wound healing, and in HS. The Atomic Force Microscope (AFM) includes an optical head (laser and position detector) and glass fluid chamber; cantilevers are mounted on a piezo-electric positioner. Piconewton molecular forces of complex metrical mixtures can be measured; matrix compression (or pulling) with siliconnitride tips generates force-extension curves from which elastic deformation is calculated. The present inventors have studied the interstitial matrix extracted from aorta and aortic vascular smooth muscle cells (VSMCs) in dissecting aneurysm (DAA). Thus, AFM can be used to study the interstitial matrix of skin. The results of repeated deformations (automated by the AFM) allows the construction of histograms for statistical analysis (data not shown); hence, the method allows for rapid and relatively uncomplicated analysis of subtle alterations in native matrix formed in vitro, or extracted from an in vivo sample.

Unexpectedly, the data shown herein using skin fibroblasts from scars (see below) show profound alterations in cell-matrix molecules at μM AEEA exposures. Thus, AEEA and its analogs have profound and relatively specific effects on matrix production, at low doses not toxic to cells in in vitro studies using hypertrophic scar cells isolated from patients.

AFM compression studies. AFM studies on cells cultured on coverslips in 24-well for 7-14 days provide adequate matrix films for AFM analysis. AFM study of the mechanical properties of extracellular matrix over a range of both in vivo and in vitro exposures to AEEA can be accomplished by compression experiments. In vitro matrix scaffold can be prepared by decellularization; and in vivo extracellular matrix will be prepared from isolated collagen or elastin extracts of native matrix (in phosphate-buffered saline at 10-100 μg/ml) as films of consistent thickness adsorbed onto freshly evaporated gold coated mica coverslips.

Preparation of Decellularized Matrix Scaffold, or Extracellular Matrix (ECM): The methods for isolation and characterization of the matrix of skin cells (fibroblastic-type cells) derived from normal (N Fb) and those derived from hypertrophic scar (HS Fb), as well as an embryonic fibroblast (E Fb) as a further control for comparison by the present inventors; these basic methods can be followed in the characterization of mechanism(s) of HS. Briefly, fibroblast-like cells are cultured on 13 mm diameter Nunc™ Thermanox™ Coverslips (Catalog #174950) in 24-well cell culture plates in DMEM supplemented with 13% FCS, antibiotics, and 50 μg/ml of sodium ascorbate; cells are seeded at the number that cell density reaches 70% confluence in 24 hours. AEEA treatments start before the formation of ECM, at the second day post passage. Sodium ascorbate, which is the crucial cofactor of lysyl oxidase (LOX), lysyl hydroxylase, and proline hydroxylase (to be assayed), is added daily, 5 days/week, to stimulate ECM assembly. AEEA is changed with culture media (every 3 days). It was found that SMCs produce abundant ECM in 10 days. After 14 days of culture, the resulting tissue sheets are gently rinsed twice with PBS, and then incubated in sterile deionized water for 20 minutes at 4° C. to lyse the cells with hypotonic condition (decellularization). Matrix is rinsed free of cell debris, and ECM samples are kept overnight at 4° C. The next day, water is replaced with PBS, and the preparation is ready for AFM, or other biochemical, molecular or proteomic studies as described below.

Mechanical properties of the films will be measured using an AFM instrument capable of measuring forces in the range of 10-10,000 piconewtons (pN). Samples can be compressed by a cantilever and force vs. displacement measured during repeated compression cycles. We will use spherical tips with a borosilicate glass sphere glued to the end of V-shaped tipless silicon nitride cantilevers (radius=10 μm). The spring constant of each individual cantilever will be calculated using the equipartition theorem. The rms force noise (1-kHz bandwidth) will typically be ~10 pN. Elastic deformation will utilize the Young modulus, plotting the cantilever indentation vs. the measured compression force, according to Hertz, 1881 (formula not shown). The extensibility of the different films will be analyzed using the worm-like chain (WLC) model of polymer elasticity. Controls will include mica coverslip alone (hardest sample), agarose films (for which the elastic modulus is known) and a synthetic elastin film. Agarose gels are prepared with 2.0%, 2.5% and 3.0% (w/w) agarose in water formed on plastic rings (inner ring diameter ~5 mm; thickness ~0.1 mm), which are glued onto stainless steel disks.

Statistical Analysis; AFM: Multiple sample compressions of a single film will be performed, histograms of persistence and contour lengths constructed, and parameters of distensibility, elasticity, and inter-molecular interactions derived from force-extension curves; these parameters are known, important characteristics of the inelastic, firm ECM of HS. Histograms of parameters will be compared by ANOVA with the Wilconox test. Standard curve-fitting and regression analyses (SigmaStat, San Rafael, Calif.) are appropriate for comparison of such physiologic data (e.g., degree of "stiffness," elasticity, etc.). Note that degree of morphologic injury will also be analyzed using an established grading system.

AFM "pulling" studies: Another alternative is to "pull" samples (rather than "compress"); matrix samples could be "pulled" with pyramidal silicon-nitride tips to generate force-extension curves that are similarly analyzed. A great deal can be learned about inter- and intra-molecular interactions from experiments in which aggregates of molecules are pulled.

AEEA (or analog) affect collagen and ECM production and formation (in normal skin cells vs. HS cells) by defining myofibroblastic dysregulation of α-SMA, fibronectin, TGF-β1, TGF-β1/Smad signaling, and other potential matrix components. Additional AEEA analogs can be studied for those showing effects similar to AEEA.

HS is a pathologic process in which the normal healing of skin goes awry, resulting in abnormal scar matrix. The normal healing process involves a host of inflammatory mechanisms initially, followed by the laying down of mature intercellular matrix. It is thought that fibroblast-like cells begin the elaboration of scar interstitial elements, however it is now generally accepted that the more mature synthetic cells during the later healing phase are fibroblast-like cells with myoblastic qualities. Myofibroblasts, which are fibroblastic cells expressing α-smooth muscle myosin.

Figure 3:
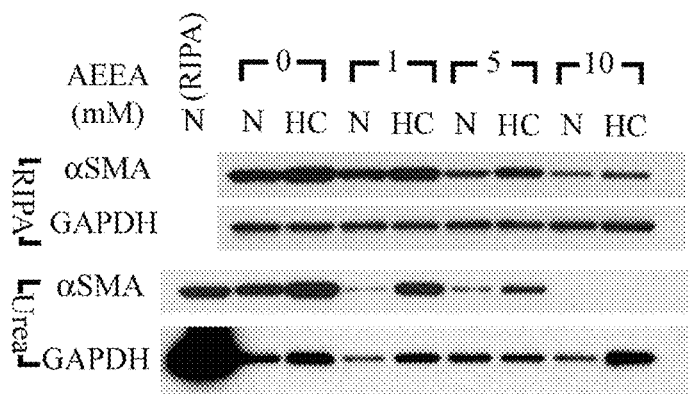
FIG. 3 shows the "high dose" dose-response: Cells grown in 1-10 mM AEEA, 14 days; ECM extracted by standard denaturing method (RIPA followed by Urea). Normal (N) and HS skin fibroblasts from single HS patient; downregulation of α-SMA in cells from both N and HS indicates loss of myofibroblast phenotype. GAPDH is loading control.

The dysregulation of myofibroblasts and accordingly the up-regulation of α-SMA expression are theorized to be a key mechanism leading to the formation of HS, but not a limitation of the present invention. It has been demonstrated that early wound cells, i.e., granulation tissue, function in many respects similar to smooth muscle, hence the term "myofibroblasts". Scar tissue's capacity to contract, as well as react to adrenergic antagonists, suggests that catecholamine levels and specific receptors are functional in the myofibroblasts during early wound healing. The present inventors found that at a higher level of AEEA exposure showed a loss of α-SMA in both normal scar cells and HS cells (FIG. 3). FIG. 3 shows the "high dose" dose-response: Cells grown in 1-10 mM AEEA, 14 days; ECM extracted by standard denaturing method (RIPA followed by Urea). Normal (N) and HS skin fibroblasts from single HS patient; downregulation of α-SMA in cells from both N and HS indicates loss of myofibroblast phenotype. GAPDH is loading control. This down regulation of α-SMA indicates a dramatic phenotypic change, away from the myofibroblastic phenotype. Surprisingly, down regulation of α-SMA was dose-dependent, and AEEA's effect appeared most pronounced in HS cells.

Detailed time course and dose response studies using the inventors' established non-denaturing (native) gel techniques can be used to test the effects of AEEA on stability of α-SMA protein. Immunohistological studies of α-SMA in cultured cells and matrix on coverslips (multiphoton microscopy; confocal microscopy, SEM) upon exposure to AEEA and its analogs can also be conducted. Further, α-SMA mRNA can be measured by real-time PCR or Northern blotting. If the α-SMA transcription is down-regulated, the molecular mechanism can then be dissected. For example, the mRNA for α-SMA can be tested for stability, to further understand whether the decrease of α-SMA transcripts is due to the decrease of mRNA synthesis, or increase of mRNA degradation. Actinomycin D can be used to inhibit transcription, and then time course of the changes of α-SMA transcripts can be tested. If the change of the α-SMA mRNA stability cannot account on all the mRNA down-regulation, the mechanisms of the down-regulation of transcription can be determined. TGF-β1 levels (active+latent forms of TGF-β1) will be measured in conditioned culture media using TGF-β1 ELISA kits for humans (R&D Systems, USA). The abundance of Smurf2 protein will be assayed by Western blotting. If α-SMA transcripts decrease much faster, we will then perform RNAseq analysis, which is a recently developed approach to transcriptome profiling that uses deep-sequencing technologies to provide a far more precise measurement of levels of transcripts and their isoforms than other methods, and detection of non-coding small RNA, including microRNA, which may result in mRNA degradation. Electrophoretic mobility shift assays (EMSA) can be performed to test it there is any band shift caused by changes of cellular proteins, including transcription factors, which bind to the α-SMA gene promoter. If a band shift is detected, then the transcription factors/DNA binding proteins that bind to the α-SMA gene promoter will be characterized by pulling down the DNA-protein complex with a biotin-labelled α-SMA gene promoter DNA fragment and streptavidin beads followed by analysis.

Low Dose AEEA; Data re: Collagen: Using the cells obtained from the severely burned patient, as detailed above, the inventors probed the alterations in intercellular matrix produced in vitro by basic biochemical and Western blot methods. The inventors focused on HS fibroblasts, specifically: collagen types 1 and 3, as well as α-SMA; either SMA or GAPDH served as a loading control (see FIGS. 4-7). Isolation of matrix was done by established methods (detailed methods are given below).

FIG. 3 shows the "high dose" dose-response: Cells grown in 1-10 mM AEEA, 14 days; ECM extracted by standard denaturing method (RIPA followed by Urea). Normal (N) and HS skin fibroblasts from single HS patient; downregulation of α-SMA in cells from both N and HS indicates loss of myofibroblast phenotype. GAPDH is loading control.

Figure 4:
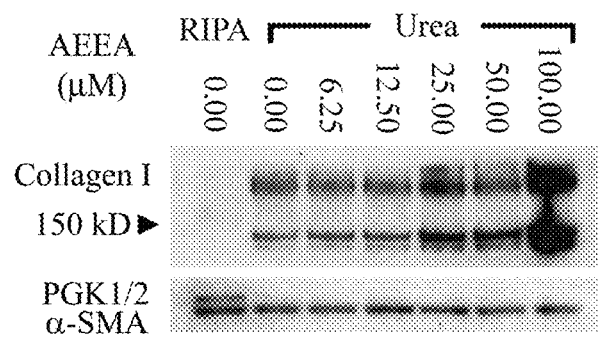
FIG. 4 shows a sequential extraction of ECM by denaturing method (RIPA followed by Urea): Increasing Extractability of Collagen 1; doses are many-fold lower than data shown in previous submission; 14 day exposure. Note, α-SMA is not down-regulated as it was at higher (mM) doses; see FIG. 3. PGK1/2 is fraction marker.
Figure 5:
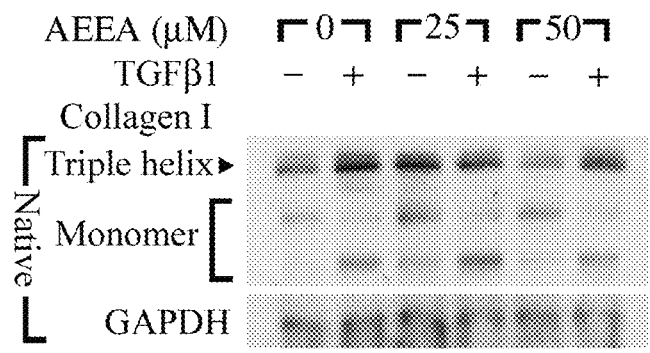
FIG. 5 shows a native gel after a 7 day exposure of HS cells to AEEA. Native lysis buffer uses digitonin; see text. Collagen tertiary structure revealed (triple helix of ~300 kD vs. monomers). TGFβ1 treatment (4 days) increases mature (triple helical) structure, while changing monomer ratio, an effect that is mimicked by AEEA-alone at 25 μM but not at 50 μM (see text and FIG. 7 re: fibronectin). TGFβ1 effect appears attenuated by 50 μM AEEA.

FIG. 4 shows a sequential extraction of ECM by denaturing method (RIPA followed by Urea): Increasing Extractability of Collagen 1; doses are many-fold lower than data shown in previous submission; 14 day exposure. Note, α-SMA is not down-regulated as it was at higher (mM) doses; see FIG. 3. PGK1/2 is fraction marker. FIG. 4 shows that collagen type 1, which is the predominant mature collagen in most tissues, including normal scars and mature hypertrophic scars, was much more extractable (soluble) in both RIPA (not shown) and urea lysis buffer in the serial extractions. This markedly increased extractability of collagen type 1 was found to occur in a dose dependent manner at AEEA concentrations as low as 25 µM (2 fold by densitometry) and 5-fold at 100 µM. These collagen aberrations were then examined with non-denaturing, or "native" gels (FIG. 5). "Native" or "non-denaturing" gel electrophoresis is run in non-denaturing conditions, i.e., in the absence of any charged denaturing agents, such as SDS; and reducing agent. Native gel allows for the protein's natural structure to be maintained. Thus, the physical size of the folded or assembled complex affects mobility. In SDS-PAGE, the electrophoretic mobility of proteins depends primarily on their molecular mass alone; in native gel the mobility also depends on both the protein's charge and its hydrodynamic size. The native lysis buffer used contains: 50 mM Tris-HCl, pH 7.5; 150 mM NaCl and 1% Digitonin.

Using these methods, alterations in three important mediators of cell-to-matrix interaction were found, namely: fibronectin, the integrins, and N-cadherin (a discussion of importance of these molecules, and their role in HS is described in further detail below). In these studies the inventors investigated the role of one of the most important regulators of scarring and HS-TGFβ1.

FIG. 5 shows that after 7 days (TGFβ1 exposure, last 4 days) a TGFβ1 effect of 10- and 16-fold increases in triple helical collagen (mature, intact intramolecular bonds) at 0.0 (control) and 25 µM AEEA, respectively. However this finding is not present at 50 µM AEEA. Following 25 µM AEEA alone, a 6-fold increase was seen. The triple helical structure in the presence of both AEEA and TGFβ1 appeared relatively diminished. These complex results indicate that multiple mechanisms are involved with regard to the effects of AEEA and TGFβ1 on the tertiary intramolecular structure of mature collagen type 1.

Figure 6:
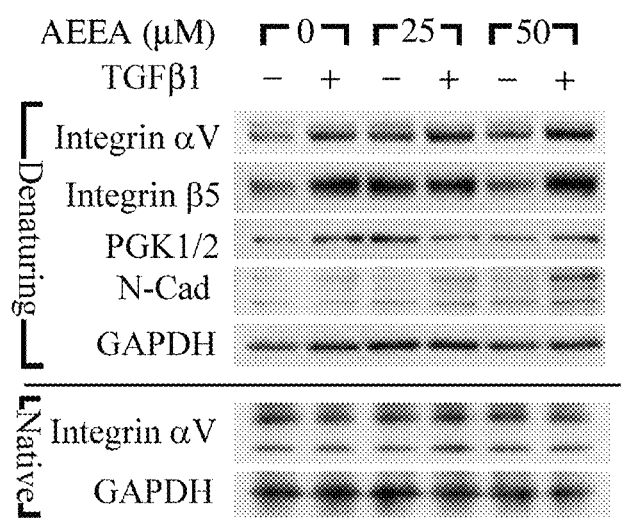
FIG. 6 shows a denaturing gel, in which TGFβ1 and AEEA have similar effect, increasing Integrins αV and β5, which are involved in HS pathophysiology. Extractable N-Cadherin, a critical trans-membrane adhesion protein, also increased, especially with exposure to both AEEA and TGFβ1. Results show that AEEA disrupts these critical ligands for collagen and interstitial matrix production that are beneficial in altering the course of HS. In the native gel, intensities of integrin bands are not changed in a parallel fashion to that in denaturing gels, which may be the result of intramolecular alterations.

FIG. 6 shows a denaturing gel, in which TGFβ1 and AEEA have similar effect, increasing Integrins αV and β5, which are involved in HS pathophysiology. Extractable N-Cadherin, a critical trans-membrane adhesion protein, also increased, especially with exposure to both AEEA and TGFβ1. Results show that AEEA disrupts these critical ligands for collagen and interstitial matrix production that are beneficial in altering the course of HS. In the native gel, intensities of integrin bands are not changed in a parallel fashion to that in denaturing gels, which may be the result of intramolecular alterations. In FIG. 6, the effect of AEEA on fibronectin, integrins αV and β5, and N-cadherin is examined, which have all been implicated in the development of HS. In a denaturing gel, TGFβ1 and AEEA exposure has a similar effect of increasing extractability of integrins and, to some extent, N-cadherin. However, native gels of the same samples indicates that the band intensities are not altered in a parallel fashion to that in denaturing gels, again suggesting that AEEA and TGFβ1 change the intramolecular structure. Most interesting are interactions between AEEA and TGFβ1 with regard to HS cell expression of fibronectin, a critical molecule in cell adhesion, growth, migration, and differentiation, which is implicated in HS.

Figure 7:
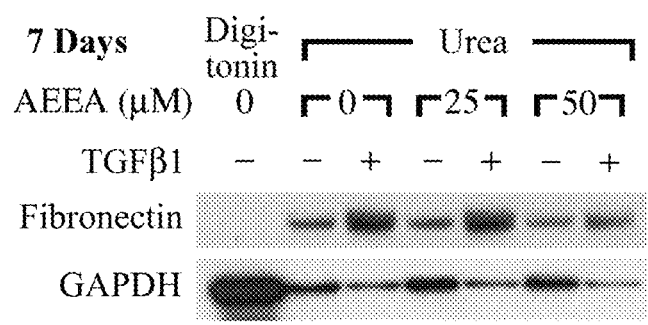
FIG. 7 shows a denaturing gel following digitonin is used to demonstrate fibronectin (cell exposure as in FIG. 5). Increased extractability of fibronectin induced by TGFβ1, with little effect of AEEA at 25 or 50 μM. However, the TGFβ1 enhancement of fibronectin is blocked by 50 μM AEEA (last two lanes). Fibronectin, a critical cell adhesion molecule, is implicated in HS. The results of FIGS. 5 and 7 suggest that TGFβ1 effect, known to accompany myofibroblast formation in HS, may be attenuated by AEEA. See text for densitometric analysis, FIGS. 3-7.

FIG. 7 shows a denaturing gel following digitonin is used to demonstrate fibronectin (cell exposure as in FIG. 5). Increased extractability of fibronectin induced by TGFβ1, with little effect of AEEA at 25 or 50 µM. However, the TGFβ1 enhancement of fibronectin is blocked by 50 µM AEEA (last two lanes). Fibronectin, a critical cell adhesion molecule, is implicated in HS. The results of FIGS. 5 and 7 suggest that TGFβ1 effect, known to accompany myofibroblast formation in HS, may be attenuated by AEEA. See text for densitometric analysis, FIGS. 3-7. FIG. 7 shows markedly increased (5-fold) extractability of fibronectin induced by TGFβ1 in denaturing gel, whereas AEEA at 25 or 50 μM had little effect. Notably, the TGFβ1 enhancement of fibronectin was blocked by 50 μM AEEA (last two lanes), suggesting that TGFβ1's effect, which regulated cell migration and accompanies myofibroblast phenotype conversion in HS, may be attenuated by AEEA.

Total collagen content of the matrix can be determined by established extraction procedures and a dye-binding method based on the specific binding of Sirius Red dye to the [Gly-X-Y]$_n$ helical structure of collagen types I to XIV. The method has virtually an exact correlation with analytic methods for hydroxyproline content. Elastin can be determined in separate samples as soluble tropoelastin utilizing a dye binding assay (Accurate Chemical Corp., Westbury, N.Y.) and as insoluble elastin by repeated salt and alkali extraction as previously described. [10, 11] The effects of AEEA on collagen and other extra-cellular protein abundances can be further evaluated by using the normal human neonatal primary dermal fibroblast (ATCC® PCS-201-010™), and normal skin fibroblasts (NS Fb), and also hypertrophic scar fibroblasts (HS Fb) derived from skin of the other clinically evident HS developed by patients. Time course and dose response studies can also be used to test the effects of AEEA on stability of those proteins, by Western blotting, to see if it is degraded more quickly in the AEEA treated cells. For Western Blot, cultured N Fb and FS Fb grown and treated with AEEA as described above can be gently washed with 4° C. pre-chilled PBS. The plate is then placed on the surface of a −20° C. ice block. Although the cross-linked collagens are not soluble, the non-cross linked collagens are extractable, depending on the strength of the extracting solution. Therefore, samples are serially extracted with RIPA buffer, urea extraction buffer and then 0.5 M acetic acid; or, with native sample buffer, as described above. Collagens not extracted in the previous steps are then extracted in acetic acid, e.g., using equal volumes of 0.5 M acetic acid. Samples are incubated at 4° C. on a shaker for 1 hour, centrifuged as above, and supernatants saved. Samples will be neutralized. The protein concentrations of the samples extracted with RIPA measured by with the DC™ protein assay kit (Bio-Rad Laboratories, Inc. USA), while the protein of remaining extracts is quantitated with the BCA protein assay (Pierce). Fractions are subjected to standard native (described above) or SDS-PAGE (Novex® NuPAGE® SDS-PAGE gel system, 4%-12% Bis-Tris Pre-Cast gels, NP0321, Invitrogen). The separated proteins were transferred to PVDF membrane (BioRad) and blocked with 3% BSA (Sigma) in TBS-T. Antibodies utilized include: collagen I (ab34710), collagen III (ab6310), α-smooth muscle actin (ab5694) and secondary antibodies included anti-rabbit and anti-mouse IgG antibodies conjugated to horseradish peroxidase (ab6721 and ab6728, respectively) from Abcam. Antibody against PGK1/2 (H-300, sc-28784) is from Santa Cruz. Signals are recorded on film (CL-XPousure™ film, Thermo Scientific) by using ECL™ Western blot detection reagents (Amersham Biosciences, RPN2209).

If the ECM proteins degrade more quickly in the AEEA treated cells, then the possible degradation pathways involved can be tested by blocking each pathway, e.g., MMPs pathway can be blocked by ilomastat (Selleck Chemicals), the ubiquitin pathway can be blocked by MG132; the calpain pathway can be blocked by E64d; etc. Immune-histological studies can also be conducted for those proteins in culture cells and matrix on coverslips (multiphoton microscopy; confocal microscopy, SEM). Lysyl oxidase (LOX) is an extracellular copper enzyme that catalyzes formation of aldehydes from lysine residues in collagen and elastin precursors. These aldehydes are highly reactive, and undergo spontaneous chemical reactions with other lysyl oxidase-derived aldehyde residues, or with unmodified lysine residues. This cross-linking in collagen and elastin is essential for stabilization of collagen fibrils and for the integrity and elasticity of mature elastin. The effects of AEEA on LOX activity and collagen cross-linking can also be determined by detecting LOX protein (Western blotting), and activity (Amplex Red Lysyl oxidase activity assay). It is also possible to measure the levels of hydroxyproline in collagen. Collagen degradation can also be determined by measuring hydroxyproline released to the culture medium according to known methods; detection of MMP activity (zymogram) and the abundance of tissue inhibitors of metalloproteinases in different fibroblasts. Total fibrillin-1 will be assayed with the fluorescent antibody technique of by Sakai et al. [42]. In cultured fibroblastic cells, profibrillin-1 conversion to fibrillin-1 will be assayed by pulse-chase metabolic labeling and analysis, after published methods. Total proteoglycans and sulphated glycosaminoglycans will be determined by a quantitative dye-binding method. Dysfunction in fibrillogenesis is expected to be reflected in inadequate type I and/or III collagens, molecular damage of collagens and or elastin, and in potential alterations in fibrillin, mechano-sensing molecules (integrins, fibronectin, cadherins, etc.), glycoproteins or other matrix proteins. In addition, tropoelastin transcripts wilcanl be quantitated by in situ hybridization of isolated fibroblastic cells at the termination of experiments; this method uses a digoxigenin-labelled probe. Morphometrically quantitated intensity of tropoelastin transcripts can be compared between control and AEEA-exposed aortic/cell matrix.

Early healing phase, or granulation tissue, is composed largely of procollagen, elastin, proteoglycans and hyaluronic acid and forms a structural repair framework to bridge the wound and allow vascular ingrowth. Myofibroblasts help initiate wound contraction and once the wound is closed the immature scar can transition into the final maturation phase, which may last several months. Lysyl oxidase (LOX) oxidizes the side chain of peptidyl lysine converting specific lysine residues to residues of α-aminoadipic-δ-semialdehyde. This posttranslational chemical change permits the covalent crosslinking of the component chains of collagen and those of elastin, thus stabilizing the fibrous deposits of these proteins in the extracellular matrix.[57] The abundant ECM is then degraded and the immature type III collagen of the early wound can be modified into mature type I collagen. The balance of synthesis and degradation of scar components shifts into a downregulation of healing to allow the final scar to gain maximum organization and strength. The multistep process of wound healing is regulated on the biochemical level by a vast array of signaling mechanisms. Families of molecules including TGF-β, mitogen-activated protein (MAP) kinases, and matrix metalloproteinases (MMPs) all work together to regulate normal wound healing. MMPs are involved in the balance by degrading extracellular matrix. MMPs also activate latent TGFβ, and hence play an important role in the control of the inflammatory response through the modification of proinflammatory cytokines, chemokines, and shedding of membrane receptors. The effector molecules that link these regulatory signals and the three phases of healing are incompletely understood. The complexity of this system, however, offers many vulnerabilities that can result in abnormal scar formation. HS is characterized by an excessive deposition of collagen, particularly collagen I, which is the main structural element of the extracellular matrix (ECM) in most tissues. Smad proteins can be examined, which are important intracellular mediators of TGF-β1 signaling. Smad ubiquitination regulatory factor 2 (Smurf2), an ubiquitin ligase for Smads, plays critical roles in the regulation of TGF-β1/Smad signaling.

Figure 8:
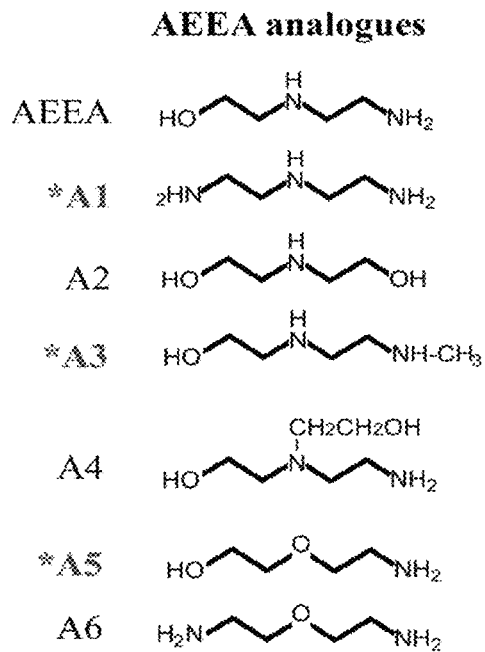
FIG. 8 shows the analogs of AEEA, based on structure-activity considerations, used with the present invention.

Due to the advantageous effect of AEEA on collagen and ECM metabolism, the inventors expanded the present invention to analogs that can also be effective, as such, related chemicals were generated via chemical structure-activity relationship studies. Thus, 12 chemical analogs of AEEA that are commercially available (FIG. 8) were tested. FIG. 8 shows the analogs of AEEA, based on structure-activity considerations, used with the present invention. Six of these compounds were tested as described hereinabove using matrix analysis of collagen I.

Figure 9:
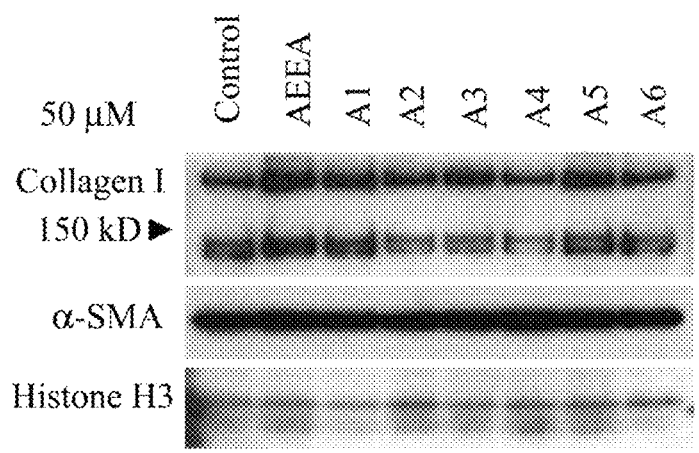
FIG. 9 shows an analysis of Collagen I extractability in human burn wound fibroblasts (from HS) cultured in 50 μM analog based on similar structure to AEEA. See chemical structures of AEEA analogs in FIG. 3 above.

FIG. 9 shows an analysis of Collagen I extractability in human burn wound fibroblasts (from HS) cultured in 50 μM analog based on similar structure to AEEA. See chemical structures of AEEA analogs in FIG. 3 above. FIG. 9 shows that at least 3 chemicals (A1, A3, and A5); each showed a 2-fold increase whereas AEEA showed 3-fold, densitometrically). Thus, the present invention also includes a method for evaluating analogs, as well as the analogs, that can be analyzed by in vitro methods for potential in vivo testing; such designed analogs serve as the drugs for HS therapy.

Values obtained for the mechanistic biochemical data, Western densitometry analyses, etc.) can be compared between paired experimental vs. exposed values using a pair-wise t-test or ANOVA for multiple groups. Curve-fitting or regression analysis (when appropriate) will use standard methods (SigmaStat, Jandel Scientific Corp., San Rafael, Calif.).

The AEEA and its analogs can be further assessed for efficacy in vivo by treatment in the most appropriate large animal model of HS (Duroc pig) as a well-known model system for burns in human patients. Besides assessing parameters of wound healing and of potential clinical importance (means of administration; dose; etc.), the mechanistic and biophysical studies described hereinabove can also be applied to HS lesions, comparing always AEEA effect on HS scarring, and on normal burn wound scarring.

Annually, 700,000-900,000 burn patients develop severe hypertrophic scarring. Since there is no effective chemotherapeutic agent for hypertrophic scars, our new finding of AEEA anti-scar effects at non-toxic concentrations is unique. A more clinical, developmental approach to testing whether AEEA or its analogs is described herein. Topical application of the AEEA and its analogs can be using the various methods described herein, including at the protein level, cellular level in vitro, or in vivo. Clinical efficacy of AEEA treatment on HS lesions, i.e. size, firmness, and other qualities will be tested in a double blind fashion. The lesions will also be subject to the biophysical, biochemical and molecular studies as taught herein.

The red Duroc pig has been deemed the best in vivo model in that it demonstrates skin anatomy and biology very similar to the human's, and develops true HS very similar to patients [61, 62]. These proposed studies are innovative in that AEEA and its analogs, which are drugs in use today can be tested for beneficial effects on pathological healing. Hence, the novelty of the present proposal is twofold: the in vivo model and the substance to be tested as an anti-HS chemotherapeutic agent.

Many in vivo models of burn injury and hypertrophic scarring have been used in a variety of animals; these include the rabbit ear, mouse, nude mouse, and a variety of pigs. Although a variety of in vivo models of HS have been used (rabbit ear model, mouse, nude mouse, a variety of pigs), the red Duroc pig has emerged as the model of HS closest to HS in human skin [61, 62]. AEEA can also be added to burn wound dressing, during the critical period of HS formation.

Small Animal Burn Model:

To assess the possibility of an adverse AEEA effect on skin or burn wound healing, a rat model of 30% scald burn was utilized. AEEA was used to treat burns (or unburned skin as sham) by localized multiple injections (5 of 0.1 ml) of AEEA at 5.0 and 50.0 mM concentrations, which are 100- or 1,000-fold of the effective concentration in our cell culture, respectively, but is only 10% concentration of the rat DAA experiments by gavage [3, 4]. (n at each condition=2, total of 12 rats. These doses would result in much higher local concentrations in s.c tissue than skin fibroblasts were exposed to in the data shown in figures herein (except for FIG. 3). The tissues showed minor hemorrhage and slight inflammation (7 days post-burn) at injection sites; histological studies show no qualitative or quantitative differences were seen between vehicle (PBS buffer) vs. AEEA sites in normal unburned skin or in full thickness burns (data not shown). This small animal burn model indicates that AEEA has no untoward localized skin or systemic effects in dose range that is well above those to be tested.

Animal (Duroc pig) Procedures: Healthy 30-40 kg (3-4 month old) castrated male Red Duroc pigs, acclimatized to the animal care facility, receive 12-16 full thickness paravertebral contact burns using an aluminum block heated to 200 degrees Celsius (for 40 seconds with a force of 0.4 kg/cm$^2$). This results in circular burns of 3.5 cm diameter (~40 cm$^2$) each, or a total body surface area burn of <15%.[63, 64] The burn will be performed under isofluorane anesthesia and analgesia (fentanyl) as established in the laboratory. The extent of acute burn (full thickness) will be confirmed by histology via punch biopsy (3.5 mm diameter) of selected areas of burn. The pig will receive adequate intravenous resuscitation and analgesia. After 24 hours, animals will no longer be restrained; they will be placed in normal pen housing within the lab. Post-operatively, the animals will receive intensive resuscitation and analgesia. Resuscitation is deemed adequate based on urine output greater than or equal to 1 cc/kg/hour. Analgesia is deemed as adequate based on clinical evaluation. To mimic the clinical setting, forty-eight hours after burn the animal undergoes wound excision and grafting. Under anesthesia and analgesia, burn wounds are excised and immediately covered with preparations of amnion. Covers will be stapled to wound edges and covered with triple-antibiotic ointment impregnated gauze and bulky pressure dressings. Staples or sutures can be used as required. Following wound excision and grafting fibrin sealant can be applied, then control or experimental (Opsite surgical gauze dressings treated with AEEA) are used. The Institutional Animal Care and Use Committee of the research locations review all handling, surgery, pain control and upkeep according to, and in full compliance with, the guidelines of the AAALAC.

In order to mimic the clinical situation of severe (full thickness) burn treatment and HS development, a single manipulation of the healing burn wound—application of AEEA to the chronic wound dressing—are tested. Results are assessed during the healing/scarring phase on days 14, 30, 60, 120. A single Duroc pig can receive up to 16 wounds, placed paravertebral along the back (dorsal) and shoulders (commonest sites of human HS) so that wound sites will be paired, i.e., left=control dressing, right=AEEA dressing. This allows for direct comparison of criteria of normal wound healing vs HS, and also controls for anatomic site, in a single animal. Given that a single pig will afford 6-8 paired samples and three dressing treatment concentrations of AEEA are to be tested, at a difference in means of 15%, a minimum of 6 pigs are needed to attain a p value≤0.05 at 95% confidence level using Lamorte's power calculations.

Administering AEEA in Dressings: AEEA and analogs are organic alcohol-amines. The chemicals are presumed nonirritant to normal skin at 10% or lower concentration. Application to wounds via routine dressings will be done during the secondary and tertiary phases of burn wound healing, continuously to day 120. The sites above allow for paired comparison; however the sites will be randomized so that all observations including histology will be blinded to the investigator. Standard burn wound dressing will be applied; control dressing will saline only whereas the experimental dressing will be soaked with a measured amount of AEEA the following dilutions with normal saline: 5.0 and 50.0 mM. AEEA is obtained directly from the manufacturer (BASF, DOW, or Sigma) at 99.9% purity; analogs are obtained from standard chemical suppliers.

Analyses of Burn Wounds: Clinical assessment at each interval will include wound photography, planimetric wound measurements, wound healing scores, hematologic parameters, and histologic assessment according to established criteria. [63] Punch biopsies (as above) will be obtained from each wound site under local anesthesia (5 mg bupivacaine applied to the biopsy site) for histological, immunohistochemical, cell culture studies (including atomic force microscopic analysis of matrix as) and biomolecular analysis on days 14, 30, 60 and 120. The outcome measures of histopathology microscopic observations made at each time point, with regard to wound necrosis/burn progression and wound interspace necrosis. The outcome measurements to be analyzed will be planimetric wound healing assessment and healing scores based on the established grading system of Branski et al. [63] that takes into account: re-epithelization, hypergranulation, hematoma and fibrin deposition, and wound histology. Measures of dermal and epidermal thickness will be made with an Olympus BX51 Research Light/fluorescent microscope with plan-apo objectives and appropriate Olympus image acquisition and morphometric software. Sections are divided into healthy tissue, wound edge, and wound center; two random fields are chosen and three measurements of dermal and epidermal thickness made. All measures will be done in a double blinded fashion, when possible. Histopathologic analysis for degree and extent of hypertrophic scarring (HS) will utilize established criteria for HS in standard histologic preparations (well-organized, wavy type III collagen bundles oriented parallel to epidermis surface with abundant nodules of myofibroblasts; plentiful acidic mucopolysaccharide). Dr. Boor, a long-time member of both the clinical and research staff of the Shriners Burns Hospital, is a pathologist with long experience in the histopathologic and immunohistochemical study of burns in patients. Besides routine pathological examination of the biopsies in hematoxylin & eosin and trichrome stained slides, immunocytochemistry will be performed for standard markers of fibroblast/myofibroblast cell types, as well as inflammatory markers as needed. Results of Aim #2b (mechanistic studies) will guide molecular biologic tissue analyses, emphasizing ECM proteins such as fibronectin, integrins, cadherins, and MMPs.

Statistical Analysis: Outcome parameters obtained by gross and microscopic studies will be analyzed at all-time points. Analysis of each outcome with be by mixed analysis of variance with relation to treatment, blocking on subject to account for repeated measures on two sides of each rat. Continuous outcomes (dermal thickness) will be assessed for normality by normal quantile plots and transformed to an improved approximation of normality if appropriate, with results inverted. Count outcomes (e.g., fibroblasts vs. myofibroblasts) will be modeled by Poisson or negative binomial models, as appropriate. Ordinal outcomes (healing scores) will be modeled by ordinal logistic regression. Differences among treatments will be assessed by Tukey-adjusted contrasts. A 95% level of confidence will be assumed, with alpha set at 0.05. As described above for AFM, standard curve-fitting and regression analyses will compare AFM physiologic and degree of morphologic injury based on the established grading system.

Using the model system during the critical period of HS proliferation experimental wounds will develop characteristics of HS. The potential for absorbing of the chemical from a cutaneous application is unknown. Little systemic effect or toxicity from the application of AEEA locally is expected. Based on previous, extensive work giving AEEA at high doses (gms/kg) by gavage to pregnant rat dams during their last trimester, and on the preliminary small animal (rat) experiment (above), side effect locally are not expected. Long term chronic occupational exposure to soldering fluxes which contain AEEA has been reported to result in dermatitis, [65] though neither the degree of severity nor the extent of exposure has been described. Besides clinical monitoring, biopsies will be assessed for indications of dermatitis, necrosis or overt deterioration of the grafted area, surrounding inflammation or skin reaction. Depending on the clinical effect, the dose can be increased or dropped and doses raised or lowered, based on standard clinical judgment. If toxic effects are seen, AEEA dressing can be discontinued and specific wounds can receive local or systemic treated as deemed necessary in view of standard clinical judgement. Alternative methods include the "comb" burn method in which AEEA could be injected subcutaneously (s.c.) to assess adverse/positive effects on HS. If deemed necessary in distinguishing HS characteristics, special HS markers could be used, e.g., positive proliferating cell nuclear antigen (PCNA); high p53-level; low ATP expression. Other Alternative Methods: 1) metabolic tracer studies to measure real time collagen turnover rates and pro- or anti-fibrotic factors that regulate fibrosis, using myofibroblastic cells isolated from tissue lesions according to established protocols; 2) studies of ECM protein cross-linking and amino acid analysis (HPLC) for hydroxyl lysine and hydroxyl proline.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Rabello, F. B., C. D. Souza, and J. A. Farina Junior, Update on hypertrophic scar treatment. Clinics (Sao Paulo), 2014. 69(8): p. 565-73.
2. Rhett, J. M., et al., Novel therapies for scar reduction and regenerative healing of skin wounds. Trends Biotechnol, 2008. 26(4): p. 173-80.
3. Xu, Y., et al., Dissecting aortic aneurysm induced by N-(2-aminoethyl) ethanolamine in rat: Role of defective collagen during development. Birth Defects Res A Clin Mol Teratol, 2014. 100(12): p. 924-33.
4. Chen, Z., et al., N-(2-Aminoethyl) Ethanolamine-Induced Morphological, Biochemical, and Biophysical Alterations in Vascular Matrix Associated With Dissecting Aortic Aneurysm. Toxicol Sci, 2015. 148(2): p. 421-32.
5. Ingber, D. E., Integrins, tensegrity, and mechanotransduction. Gravit Space Biol Bull, 1997. 10(2): p. 49-55.
6. Chen, Z., et al., N-(2-Aminoethyl) Ethanolamine Induced Morphological, Biochemical and Biophysical Alterations in Vascular Matrix Associated with Dissecting Aortic Aneurysm. Toxicol Sci, 2015.
7. Xu, Y., et al., Dissecting aortic aneurysm induced by N-(2-aminoethyl) ethanolamine in rat: Role of defective collagen during development. Birth Defects Res A Clin Mol Teratol, 2014.
8. Gong, B., et al., Chemical-induced, nonlethal, developmental model of dissecting aortic aneurysm. Birth Defects Res A Clin Mol Teratol, 2006. 76(1): p. 29-38.
9. Zhang, Z., et al., Smad ubiquitination regulatory factor 2 expression is enhanced in hypertrophic scar fibroblasts from burned children. Burns, 2012. 38(2): p. 236-46.
10. Langford, S. D., et al., Developmental vasculotoxicity associated with inhibition of semicarbazide-sensitive amine oxidase. Toxicol Appl Pharmacol, 1999. 155(3): p. 237-44.
11. Langford, S. D., M. B. Trent, and P. J. Boor, Semicarbazide-sensitive amine oxidase and extracellular matrix deposition by smooth-muscle cells. Cardiovasc Toxicol, 2002. 2(2): p. 141-50.
12. Davidson, J. M., et al., Ascorbate differentially regulates elastin and collagen biosynthesis in vascular smooth muscle cells and skin fibroblasts by pretranslational mechanisms. J Biol Chem, 1997. 272(1): p. 345-52.
13. Bourget, J. M., et al., Human fibroblast-derived ECM as a scaffold for vascular tissue engineering. Biomaterials, 2012. 33(36): p. 9205-13.
14. Florin, E. L., V. T. Moy, and H. E. Gaub, Adhesion forces between individual ligand-receptor pairs. Science, 1994. 264(5157): p. 415-7.
15. Marko, J. F. and E. D. Siggia, Statistical mechanics of supercoiled DNA. Phys Rev E Stat Phys Plasmas Fluids Relat Interdiscip Topics, 1995. 52(3): p. 2912-2938.
16. Mithieux, S. M., J. E. Rasko, and A. S. Weiss, Synthetic elastin hydrogels derived from massive elastic assemblies of self-organized human protein monomers. Biomaterials, 2004. 25(20): p. 4921-7.

17. Oberhauser, A. F., et al., Stepwise unfolding of titin under force-clamp atomic force microscopy. Proc Natl Acad Sci USA, 2001. 98(2): p. 468-72.
18. Oberhauser, A. F., et al., The mechanical hierarchies of fibronectin observed with single-molecule AFM. J Mol Biol, 2002. 319(2): p. 433-47.
19. Woodcock, S. E., W. C. Johnson, and Z. Chen, Collagen adsorption and structure on polymer surfaces observed by atomic force microscopy. J Colloid Interface Sci, 2005. 292(1): p. 99-107.
20. Taatjes, D. J., A. S. Quinn, and E. G. Bovill, Imaging of collagen type III in fluid by atomic force microscopy. Microsc Res Tech, 1999. 44(5): p. 347-52.
21. Oberhauser, A. F., et al., The molecular elasticity of the extracellular matrix protein tenascin. Nature, 1998. 393 (6681): p. 181-5.
22. Oberhauser, A. F., et al., Single protein misfolding events captured by atomic force microscopy. Nat Struct Biol, 1999. 6(11): p. 1025-8.
23. Wang, L., et al., Manipulating glutathione-S-transferases may prevent the development of tolerance to nitroglycerin. Cardiovasc Toxicol, 2006. 6(2): p. 131-44.
24. Langford, S. D., M. B. Trent, and P. J. Boor, Cultured rat vascular smooth muscle cells are resistant to methylamine toxicity: no correlation to semicarbazide-sensitive amine oxidase. Cardiovasc Toxicol, 2001. 1(1): p. 51-60.
25. Leask, A., Potential therapeutic targets for cardiac fibrosis: TGFbeta, angiotensin, endothelin, CCN2, and PDGF, partners in fibroblast activation. Circ Res, 2010. 106(11): p. 1675-80.
26. Hinz, B. and G. Gabbiani, Cell-matrix and cell-cell contacts of myofibroblasts:
role in connective tissue remodeling. Thromb Haemost, 2003. 90(6): p. 993-1002.
27. Nedelec, B., et al., Control of wound contraction. Basic and clinical features. Hand Clin, 2000. 16(2): p. 289-302.
28. Penn, J. W., A. O. Grobbelaar, and K. J. Rolfe, The role of the TGF-beta family in wound healing, burns and scarring: a review. Int J Burns Trauma, 2012. 2(1): p. 18-28.
29. Wang, Z., M. Gerstein, and M. Snyder, RNA-Seq: a revolutionary tool for transcriptomics. Nat Rev Genet, 2009. 10(1): p. 57-63.
30. Kliment, C. R., et al., A novel method for accurate collagen and biochemical assessment of pulmonary tissue utilizing one animal. Int J Clin Exp Pathol, 2011. 4(4): p. 349-55.
31. Caputo, I., et al., An acetic acid-based extraction method to obtain high quality collagen from archeological bone remains. Anal Biochem, 2012. 421(1): p. 92-6.
32. Lopez, B., et al., Role of lysyl oxidase in myocardial fibrosis: from basic science to clinical aspects. Am J Physiol Heart Circ Physiol, 2010. 299(1): p. H1-9.
33. Csiszar, K., Lysyl oxidases: a novel multifunctional amine oxidase family. Prog Nucleic Acid Res Mol Biol, 2001. 70: p. 1-32.
34. Gacheru, S. N., et al., Structural and catalytic properties of copper in lysyl oxidase. J Biol Chem, 1990. 265(31): p. 19022-7.
35. Kagan, H. M. and W. Li, Lysyl oxidase: properties, specificity, and biological roles inside and outside of the cell. J Cell Biochem, 2003. 88(4): p. 660-72.
36. Palamakumbura, A. H. and P. C. Trackman, A fluorometric assay for detection of lysyl oxidase enzyme activity in biological samples. Anal Biochem, 2002. 300(2): p. 245-51.
37. Sylvester, A., et al., Nanoparticles for localized delivery of hyaluronan oligomers towards regenerative repair of elastic matrix. Acta Biomater, 2013. 9(12): p. 9292-302.
38. Zork, N. M., et al., A systematic evaluation of collagen cross-links in the human cervix. Am J Obstet Gynecol, 2014.
39. Li, Z. J. and S. M. Kim, The application of the starfish hatching enzyme for the improvement of scar and keloid based on the fibroblast-populated collagen lattice. Appl Biochem Biotechnol, 2014. 173(4): p. 989-1002.
40. Creemers, L. B., et al., Microassay for the assessment of low levels of hydroxyproline. Biotechniques, 1997. 22(4): p. 656-8.
41. Ulrich, D., et al., Matrix metalloproteinases and tissue inhibitors of metalloproteinases in patients with different types of scars and keloids. J Plast Reconstr Aesthet Surg, 2010. 63(6): p. 1015-21.
42. Sakai, L. Y. and D. R. Keene, Fibrillin: monomers and microfibrils. Methods Enzymol, 1994. 245: p. 29-52.
43. Kielty, C. M. and C. A. Shuttleworth, Abnormal fibrillin assembly by dermal fibroblasts from two patients with Marfan syndrome. J Cell Biol, 1994. 124(6): p. 997-1004.
44. Raghunath, M., et al., Carboxy-terminal conversion of profibrillin to fibrillin at a basic site by PACE/furin-like activity required for incorporation in the matrix. J Cell Sci, 1999. 112 (Pt 7): p. 1093-100.
45. Aoyagi, M., et al., Smooth muscle cell proliferation, elastin formation, and tropoelastin transcripts during the development of intimal thickening in rabbit carotid arteries after endothelial denudation. Histochem Cell Biol, 1997. 107(1): p. 11-7.
46. Sarrazy, V., et al., Integrins alphavbeta5 and alphavbeta3 promote latent TGF-beta1 activation by human cardiac fibroblast contraction. Cardiovasc Res, 2014. 102(3): p. 407-17.
47. Asano, Y., et al., Involvement of alphavbeta5 integrin in the establishment of autocrine TGF-beta signaling in dermal fibroblasts derived from localized scleroderma. J Invest Dermatol, 2006. 126(8): p. 1761-9.
48. Asano, Y., et al., Increased expression of integrin alphavbeta5 induces the myofibroblastic differentiation of dermal fibroblasts. Am J Pathol, 2006. 168(2): p. 499-510.
49. Agarwal, S. K., Integrins and cadherins as therapeutic targets in fibrosis. Front Pharmacol, 2014. 5: p. 131.
50. Annes, J. P., J. S. Munger, and D. B. Rifkin, Making sense of latent TGFbeta activation. J Cell Sci, 2003. 116(Pt 2): p. 217-24.
51. Taipale, J., et al., Latent transforming growth factor-beta 1 and its binding protein are components of extracellular matrix microfibrils. J Histochem Cytochem, 1996. 44(8): p. 875-89.
52. Nunes, I., et al., Latent transforming growth factor-beta binding protein domains involved in activation and transglutaminase-dependent cross-linking of latent transforming growth factor-beta. J Cell Biol, 1997. 136(5): p. 1151-63.
53. Dallas, S. L., et al., Fibronectin regulates latent transforming growth factor-beta (TGF beta) by controlling matrix assembly of latent TGF beta-binding protein-1. J Biol Chem, 2005. 280(19): p. 18871-80.
54. Hinz, B., The extracellular matrix and transforming growth factor-beta1: Tale of a strained relationship. Matrix Biol, 2015. 47: p. 54-65.
55. Boo, S. and L. Dagnino, Integrins as Modulators of Transforming Growth Factor Beta Signaling in Dermal Fibroblasts During Skin Regeneration After Injury. Adv Wound Care (New Rochelle), 2013. 2(5): p. 238-246.

56. Barnes, J. L. and Y. Gorin, Myofibroblast differentiation during fibrosis: role of NAD(P)H oxidases. Kidney Int, 2011. 79(9): p. 944-56.
57. Lucero, H. A. and H. M. Kagan, Lysyl oxidase: an oxidative enzyme and effector of cell function. Cell Mol Life Sci, 2006. 63(19-20): p. 2304-16.
58. Slemp, A. E. and R. E. Kirschner, Keloids and scars: a review of keloids and scars, their pathogenesis, risk factors, and management. Curr Opin Pediatr, 2006. 18(4): p. 396-402.
59. Zhang, K., et al., Increased types I and III collagen and transforming growth factor-beta 1 mRNA and protein in hypertrophic burn scar. J Invest Dermatol, 1995. 104(5): p. 750-4.
60. Li, C., et al., MiR-10a and miR-181c regulate collagen type I generation in hypertrophic scars by targeting PAI-1 and uPA. FEBS Lett, 2015. 589(3): p. 380-9.
61. Domergue, S., C. Jorgensen, and D. Noel, Advances in Research in Animal Models of Burn-Related Hypertrophic Scarring. J Burn Care Res, 2014.
62. Travis, T. E., et al., Biphasic Presence of Fibrocytes in a Porcine Hypertrophic Scar Model. J Burn Care Res, 2014.
63. Branski, L. K., et al., A porcine model of full-thickness burn, excision and skin autografting. Burns, 2008. 34(8): p. 1119-27.
64. Chan, Q. E., et al., The correlation between time to skin grafting and hypertrophic scarring following an acute contact burn in a porcine model. J Burn Care Res, 2012. 33(2): p. e43-8.
65. Goh, C. L., Occupational dermatitis from soldering flux among workers in the electronics industry. Contact Dermatitis, 1985. 13(2): p. 85-90.

What is claimed is:

1. A pharmaceutical liposome formulation comprising: a N-(2-aminoethyl) ethanolamine (AEEA) and/or active analogs thereof in a liposome, wherein the N-(2-aminoethyl) ethanolamine (AEEA) and/or active analogs thereof are provided in an amount sufficient to treat or reduce scarring of the skin or eye.

2. The formulation of claim 1, wherein the AEEA and/or active analogs thereof are provided in a low dose, which is a dose that is effective to treat or reduce scarring of the skin and that reduces or does not otherwise cause dermatitis.

3. The formulation of claim 1, wherein the pH of the formulation is adjusted to reduce or prevent dermatitis.

4. The formulation of claim 1, wherein the scarring is defined further as hypertrophic scarring, scarring from burns, keloid scarring, scars that result from pimples, body piercings, tattooing, surgery, cuts and/or burns, scars associated with Classic Type Ehlers-Danlos syndrome, or scars from thermal, radiation, or traumatic skin or eye injuries that involve the deep layers of the dermis.

5. The formulation of claim 1, wherein the active analogs of AEEA are selected from at least one of:

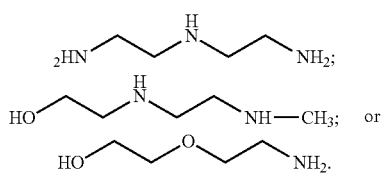

6. The formulation of claim 1, wherein the liposomes comprise one or more lipids selected from glycerophospholipids, phosphatidylcholines, phosphatidylglycerols, phosphatidylethanolamines, phosphatidylserines, phosphatidic acids, phosphatidylinositols, dimyristoyl phosphatidylglycerols, dimyristoyl phosphatidylcholines, di stearoylphosphatidylethanolamines, distearoylphosphatidylcholine, dipalmitoylphosphatidylglycerol, egg-phosphatidylcholine, egg-phosphatidylglycerol, dimyristyloxy-propyl-3-dimethyl-hydroxy ethyl ammoniums, dioleoyphosphatidyl cholines, cholesterols, cholesterol derivatives, ceramides, monosialogangliosides, sphingomyelins, cardiolipins, long chain fatty acids, one or more skin-related lipids, or mixtures thereof salts or a mixture thereof.

7. The formulation of claim 1, wherein the liposomes are further defined as comprising at least one of: a lamellarity selected from uni-, oligo-, and multi-lamellar vesicles; a size that is small, intermediate, or large; are reverse phase evaporation vesicles (VETs); are PEGylated; are targeted liposomes; and/or are stealthed liposomes.

8. The formulation of claim 1, wherein the formulation is adapted for ocular administration for the treatment of eye fibrosis selected from at least one of: exophthalmos of Grave's disease, proliferative vitreoretinopathy, anterior capsule cataract, corneal fibrosis, corneal scarring due to surgery, trabeculectomy-induced fibrosis, progressive subretinal fibrosis, and multifocal granulomatous chorioretinitis.

9. The formulation of claim 1, further comprising at least one of: a stabilizer, a penetration enhancer, a humectant, a deodorant, an aroma modifier, a sun screening agent, a sunless tanning agent, a pH adjusting agent, a sun blocking agent, a chelating agent, a preservative, an emulsifier, an occlusive agent, an emollient, a thickener, a solubilizing agent, an anti-irritant, or a colorant.

10. The formulation of claim 1, further comprising at least one penetration enhancer selected from at least one of: propylene glycol (PG), polyethylene glycol (PEG), dimethyl formamide (DMF), allantoin, urazole, N,N-dimethylacetamide (DMA), decylmethylsulfoxide, polyethylene glycol monolaurate (PEGML), propylene glycol monolaurate (PGML), Phosal glycerol monolaurate (GML), lecithin, 1-substituted azacycloheptan-2-ones, alcohols, or vegetable oils.

11. The formulation of claim 1, wherein the formulation is adapted for topical or ocular administration in the form of a cream, an ointment, a paste, a gel, a lotion, a milk, a suspension, a serum, a solution, an aerosol, a spray, a foam, a shampoo, a mousse, a serum, a swab, a pledget, a pad, a tincture, a patch, a dressing, an adhesive bandage, an oil, or drops.

12. A method of preventing or treating scar formation of the skin or eyes by administering a N-(2-aminoethyl) ethanolamine (AEEA) and/or active analogs thereof in a liposome, wherein the N-(2-aminoethyl) ethanolamine (AEEA) and/or active analogs thereof are provided in an amount sufficient to treat or reduce scarring of the skin or eye to a subject in need thereof.

13. The method of claim 12, further comprising the step of providing the AEEA and/or active analogs thereof in a low dose, which is a dose that is effective to treat or reduce scarring of the skin and that reduces or does not otherwise cause dermatitis.

14. The method of claim 12, further comprising the step of adjusting the pH of the formulation to reduce or prevent dermatitis.

15. The method of claim 12, wherein the scarring is defined further as hypertrophic scarring, scarring from burns, keloid scarring, scars that result from pimples, body piercings, tattooing, surgery, cuts and/or burns, scars associated with Classic Type Ehlers-Danlos syndrome, or scars from thermal, radiation, or traumatic skin or eye injuries that involve the deep layers of the dermis.

16. The method of claim 12, wherein the active analogs of AEEA are selected from at least one of:

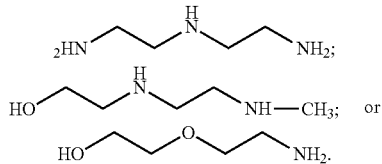

17. The method of claim 12, wherein the liposomes comprise one or more lipids selected from glycerophospholipids, phosphatidylcholines, phosphatidylglycerols, phosphatidylethanolamines, phosphatidylserines, phosphatidic acids, phosphatidylinositols, dimyristoyl phosphatidylglycerols, dimyristoyl phosphatidylcholines, di stearoylphosphatidylethanolamines, distearoylphosphatidylcholine, dipalmitoylphosphatidylglycerol, egg-phosphatidylcholine, egg-phosphatidylglycerol, dimyristyloxy-propyl-3-dimethyl-hydroxy ethyl ammoniums, dioleoyphosphatidyl cholines, cholesterols, cholesterol derivatives, ceramides, monosialogangliosides, sphingomyelins, cardiolipins, long chain fatty acids, one or more skin-related lipids, or mixtures thereof salts or a mixture thereof.

18. The method of claim 12, wherein the liposomes comprise at least one of: a lamellarity selected from uni-, oligo-, and multi-lamellar vesicles; a size that is small, intermediate, or large; are reverse phase evaporation vesicles (VETs); are PEGylated; are targeted liposomes; and/or are stealthed liposomes.

19. The method of claim 12, further comprising the step of incorporating the formulation into a wound dressing.

20. The method of claim 12, further comprising the step of adapting the formulation for ocular administration for the treatment of eye fibrosis comprises a condition selected from the group consisting of: exophthalmos of Grave's disease, proliferative vitreoretinopathy, anterior capsule cataract, corneal fibrosis, corneal scarring due to surgery, trabeculectomy-induced fibrosis, progressive subretinal fibrosis, and multifocal granulomatous chorioretinitis.

21. The method of claim 12, further comprising the step of adding at least one of: a stabilizer, a penetration enhancer, a humectant, a deodorant, an aroma modifier, a sun screening agent, a sunless tanning agent, a pH adjusting agent, a sun blocking agent, a chelating agent, a preservative, an emulsifier, an occlusive agent, an emollient, a thickener, a solubilizing agent, an anti-irritant, or a colorant.

22. The method of claim 12, further comprising the step of adding at least one penetration enhancer selected from at least one of propylene glycol (PG), polyethylene glycol (PEG), dimethyl formamide (DMF), allantoin, urazole, N,N-dimethylacetamide (DMA), decylmethylsulfoxide, polyethylene glycol monolaurate (PEGML), propylene glycol monolaurate (PGML), Phosal glycerol monolaurate (GML), lecithin, 1-substituted azacycloheptan-2-ones, alcohols, or vegetable oils.

23. The method of claim 12, further comprising the step of making a formulation for topical or ocular administration in the form of a liquid, a cream, an ointment, a paste, a gel, a lotion, a milk, a suspension, a serum, a solution, an aerosol, a spray, a foam, a shampoo, a mousse, a serum, a swab, a pledget, a pad, a tincture, a patch, a dressing, an adhesive bandage, an oil, or drops.

24. A method for treating or preventing scarring of the skin or eye, comprising:
    identifying a human or animal subject in need of prevention or treatment scarring of the skin or eye; and
    providing the subject with a topical or ocular formulation comprising a therapeutically effective amount of a N-(2-aminoethyl) ethanolamine (AEEA) and/or active analogs thereof in a liposome in an amount sufficient for treating a wound to a surface tissue or a symptom thereof.

25. A method of making a formulation treating or preventing scarring of the skin or eye when provided to a subject comprising:
    obtaining a therapeutically effective amount of a N-(2-aminoethyl) ethanolamine (AEEA) and/or active analogs thereof; and
    mixing the N-(2-aminoethyl) ethanolamine (AEEA) and/or active analogs thereof in with a vehicle adapted for topical administration.

26. The method of claim 25, wherein the vehicle adapted for topical administration is defined further as comprising one or more bio-compatible polymers selected from at least one of poly(lactic-co-glycolic acid) (PLGA), poly(lactic acid), polylactide (PLA), or poly-L-lactide-co-ε-caprolactone (PLCL), one or more solvents and at least one of the N-(2-aminoethyl) ethanolamine (AEEA), and/or active analogs thereof.

27. The method of claim 25, wherein the vehicle adapted for topical administration is defined further as comprising a lipid and the lipid is formed into a liposome by:
    mixing a lipid aqueous phase with one or more lipids in the presence of the N-(2-aminoethyl) ethanolamine (AEEA) and/or active analogs thereof;
    mixing the organic phase with the lipid aqueous phase, whereby an emulsion is formed; and
    incubating the emulsion under conditions that cause the self-assembly of liposome loaded with the N-(2-aminoethyl) ethanolamine (AEEA) and/or active analogs thereof.

28. The method of claim 27, further comprising the step of mixing the organic phase with the lipid aqueous phase comprises at least one of stirring the organic phase into the lipid aqueous phase, mixing the organic phase with the lipid aqueous phase comprises vortexing, or mixing the organic phase with the lipid aqueous phase further comprises sonicating.

29. The method of claim 25, wherein the vehicle adapted for topical administration is defined further as comprising one or more lipids formed into liposomes, wherein the lipids are selected from at least one of glycerophospholipids, phosphatidylcholines, phosphatidylglycerols, phosphatidylethanolamines, phosphatidylserines, phosphatidic acids, phosphatidylinositols, dimyristoyl phosphatidylglycerols, dimyristoyl phosphatidylcholines, di stearoylphosphatidylethanolamines, distearoylphosphatidylcholine, dipalmitoylphosphatidylglycerol, egg-phosphatidylcholine, egg-phosphatidylglycerol, dimyristyloxy-propyl-3-dimethyl-hydroxy ethyl ammoniums, dioleoyphosphatidyl cholines, cholesterols, cholesterol derivatives, ceramides, monosialogangliosides, sphingomyelins, cardiolipins, long chain fatty acids, skin-related lipids or mixtures thereof salts or a mixture thereof.

30. The method of claim 25, wherein the vehicle adapted for topical administration is defined further as comprising liposomes that comprise at least one of: a lamellarity selected from uni-, oligo-, and multi-lamellar vesicles; a size that is small, intermediate, or large; are reverse phase evaporation vesicles (VETs); are PEGylated; are targeted liposomes; and/or are stealthed liposomes.

31. The method of claim 25, further comprising the step of incorporating the formulation into a wound dressing.

32. The method of claim 25, further comprising the step of adapting the formulation for ocular administration for the treatment of eye fibrosis comprises a condition selected from the group consisting of: exophthalmos of Grave's disease, proliferative vitreoretinopathy, anterior capsule cataract, corneal fibrosis, corneal scarring due to surgery, trabeculectomy-induced fibrosis, progressive subretinal fibrosis, and multifocal granulomatous chorioretinitis.

33. The method of claim 25, further comprising the step of adding at least one of: a stabilizer, a penetration enhancer, a humectant, a deodorant, an aroma modifier, a sun screening agent, a sunless tanning agent, a pH adjusting agent, a sun blocking agent, a chelating agent, a preservative, an emulsifier, an occlusive agent, an emollient, a thickener, a solubilizing agent, an anti-irritant, or a colorant.

34. The method of claim 25, further comprising the step of adding at least one penetration enhancer selected from at least one of propylene glycol (PG), polyethylene glycol (PEG), dimethyl formamide (DMF), allantoin, urazole, N,N-dimethylacetamide (DMA), decylmethylsulfoxide, polyethylene glycol monolaurate (PEGML), propylene glycol monolaurate (PGML), Phosal glycerol monolaurate (GML), lecithin, 1-substituted azacycloheptan-2-ones, alcohols, or vegetable oils.

35. The method of claim 25, further comprising the step of making a formulation for topical or ocular administration in the form of a liquid, a cream, an ointment, a paste, a gel, a lotion, a milk, a suspension, a serum, a solution, an aerosol, a spray, a foam, a shampoo, a mousse, a serum, a swab, a pledget, a pad, a tincture, a patch, a dressing, an adhesive bandage, an oil, or drops.

* * * * *